US008633351B2

(12) United States Patent
Allen et al.

(10) Patent No.: US 8,633,351 B2
(45) Date of Patent: Jan. 21, 2014

(54) GENETIC LOCI ASSOCIATED WITH CELL WALL DIGESTIBILITY IN MAIZE

(75) Inventors: Stephen M. Allen, Wilmington, DE (US); Kanwarpal Singh Dhugga, Johnston, IA (US); Stanley Luck, Wilmington, DE (US); Victor Llaca, Newark, DE (US); Bernhard Rietmann, Ibbenburen (DE); Susanne Groh, Basel (CH)

(73) Assignees: E. I. Du Pont de Nemours and Company, Wilmington, DE (US); Pioneer Hi-Bred International, Inc., Johnston, IA (US)

( * ) Notice: Subject to any disclaimer, the term of this patent is extended or adjusted under 35 U.S.C. 154(b) by 831 days.

(21) Appl. No.: 12/613,555

(22) Filed: Nov. 6, 2009

(65) Prior Publication Data

US 2010/0122370 A1 May 13, 2010

Related U.S. Application Data

(60) Provisional application No. 61/112,203, filed on Nov. 7, 2008.

(51) Int. Cl.
*A01H 1/02* (2006.01)
*A01H 1/04* (2006.01)

(52) U.S. Cl.
USPC ............................ 800/275; 800/260; 800/267

(58) Field of Classification Search
None
See application file for complete search history.

(56) References Cited

U.S. PATENT DOCUMENTS 6,506,965 B1 * 1/2003 Carolo ........................ 800/320.1
2008/0313777 A1 12/2008 Dhugga et al.

FOREIGN PATENT DOCUMENTS

WO 2008157370 12/2008

OTHER PUBLICATIONS

Marvin et al (J. Sci. Food Agric. 69: 215-221, 1995).*
Whetton R and Sederoff R, (1995) Lignin Biosynthesis. The Plant Cell, vol. 7, p. 1001-1013.
Whetten R et al., (1998) Recent Advances in Understanding Lignin Biosyntesis. Annu. Rev. Plant Physiol. Plant Mol. Biol., vol. 49, p. 585-609.

National Center for Biotechnology Information General Identifier No. 194692196, Accession No. ACF80182, Jul. 30, 2008, Yu et al., Maize Full-Length cDNA Project.
Argillier et al., (1995) Genetic variation and selection criterion for digestibility traits of forage maize. Euphytica, vol. 82, p. 175-184.
Barriere et al., (2000) Forage maize III—evaluation and prospects of genetic progress in feeding value characteristics. Fourrages, vol. 163, p. 221-238 (Abstract end of article).
Barriere, Y. et al., (2005) QTL analysis of lignification and cell wall digestibility in the Bay-0 x Shandara RIL progeny of *Arabidopsis thaliana* as a model system for forage plant. Plant Science, vol. 168, p. 1235-1245.
Caparros-Ruiz, D. et al., (2006) Isolation and characterization of a family of laccases in maize. Plant Science, vol. 171, p. 217-225.
Liang, M. et al., (2006) Expression of a putative laccase gene, ZmLAC1, in maize primary roots under stress. Plant, Cell and Environment, vol. 29, p. 746-753.
Bao, W. et al., (1993) A Laccase Associated with Lignification in Loblolly Pine Xylem. Science, vol. 260, p. 672-674.
Mechin, V. et al., (2001) Genetic Analysis and QTL Mapping of Cell Wall Digestibiity and Lignification in Silage Maize. Crop Science 41, 690-697.
Grabber, J.H. et al., (2004) Genetic and molecular basis of grass cell-wall degradability. I. Lignin-cell wall matrix interactions. C.R. Biologies, vol. 327, p. 455-465.
Ralph, J. et al., (2004) Genetic and molecular basis of grass cell-wall biosynthesis and degradability. III. Towards a forage grass ideotype. C.R. Biologies, vol. 327, p. 467-479.
Shi, C. et al., (2007) identification of candidate genes associated with cell wall digestibility and eQTL (expression quantitative trait loci) analysis in a Flint x Flint maize recombinant inbred line population. BMC Genomics, vol. 8, p. 22-37.
Barriere, Y. et al., (2004) Genetic and molecular basis of grass cell wall biosynthesis and degradability. II. Lessons from brown-midrib mutants. C.R. Biologies, vol. 327, p. 847-860.
Barriere, Y. et al., (2003) Genetic variation and breeding strategies for improved cell wall digestibility in annual forage crops. A Review. Anim. Res., vol. 52, p. 193-228.
Thomas, J, et al., (2010) Cell wall phynylpropanoid-related gene expression in early maize recombinant inbred lines differing in parental alleles at a major lignin QTL position. Molecular breeding. vol. 25(1), p. 105-124.
Barriere, Y. et al., (2008) QTL mapping for lignin content, lignin monomeric composition, p-hydroxycinnamate content, and cell wall digestibility in the maize recombinant inbred line progeny F838xF286. Plant Science, vol. 174(4), p. 585-595.

* cited by examiner

*Primary Examiner* — Shubo (Joe) Zhou
*Assistant Examiner* — Keith Robinson

(57) ABSTRACT

The invention relates to methods and compositions for identifying maize plants that have increased cell wall digestibility. The methods use molecular markers to identify and select plants with increased cell wall digestibility or to identify and counter-select plants with decreased cell wall digestibility. Maize plants generated by the methods of the invention are also a feature of the invention.

9 Claims, 6 Drawing Sheets

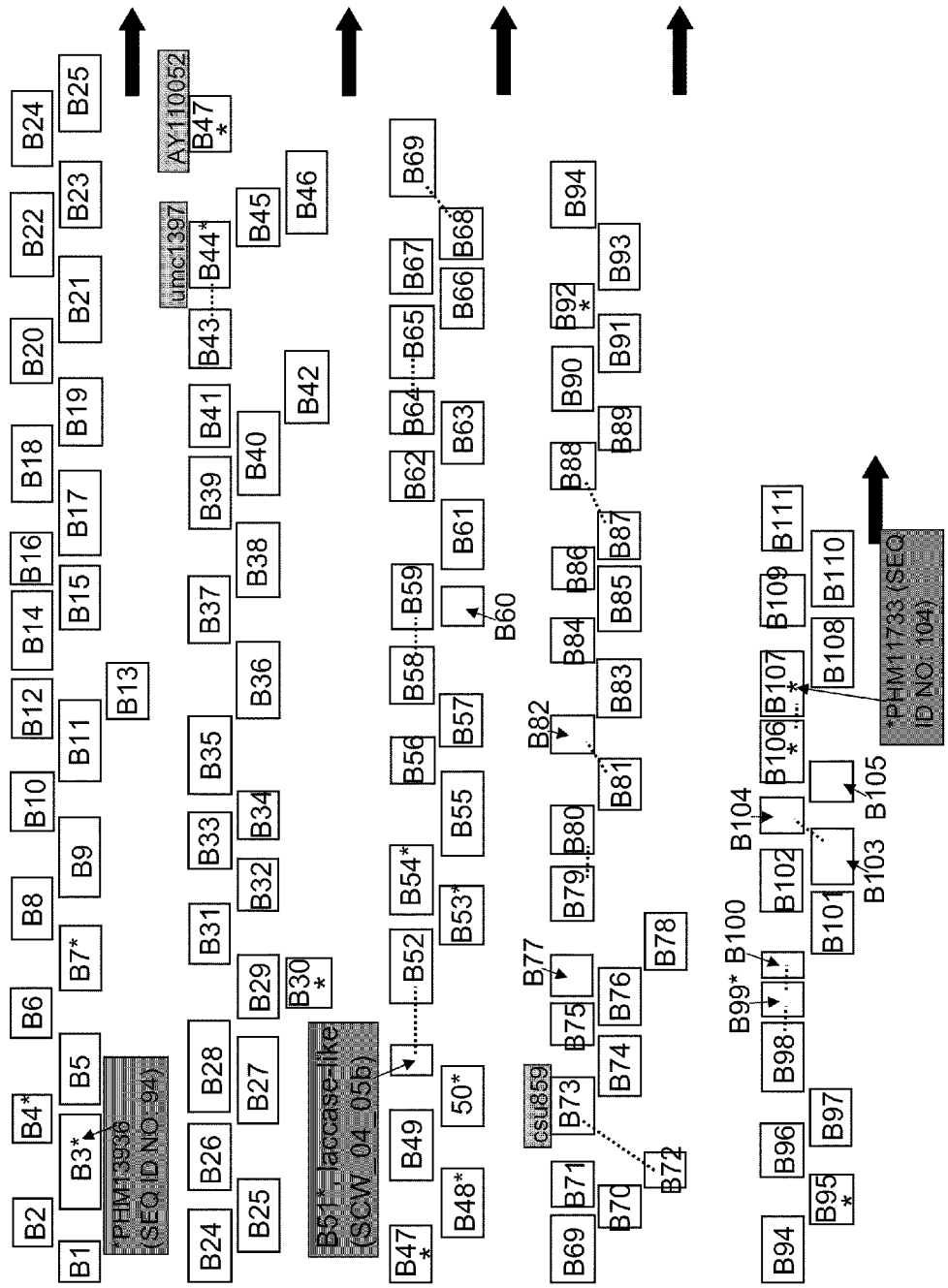
FIG 1: Physical map

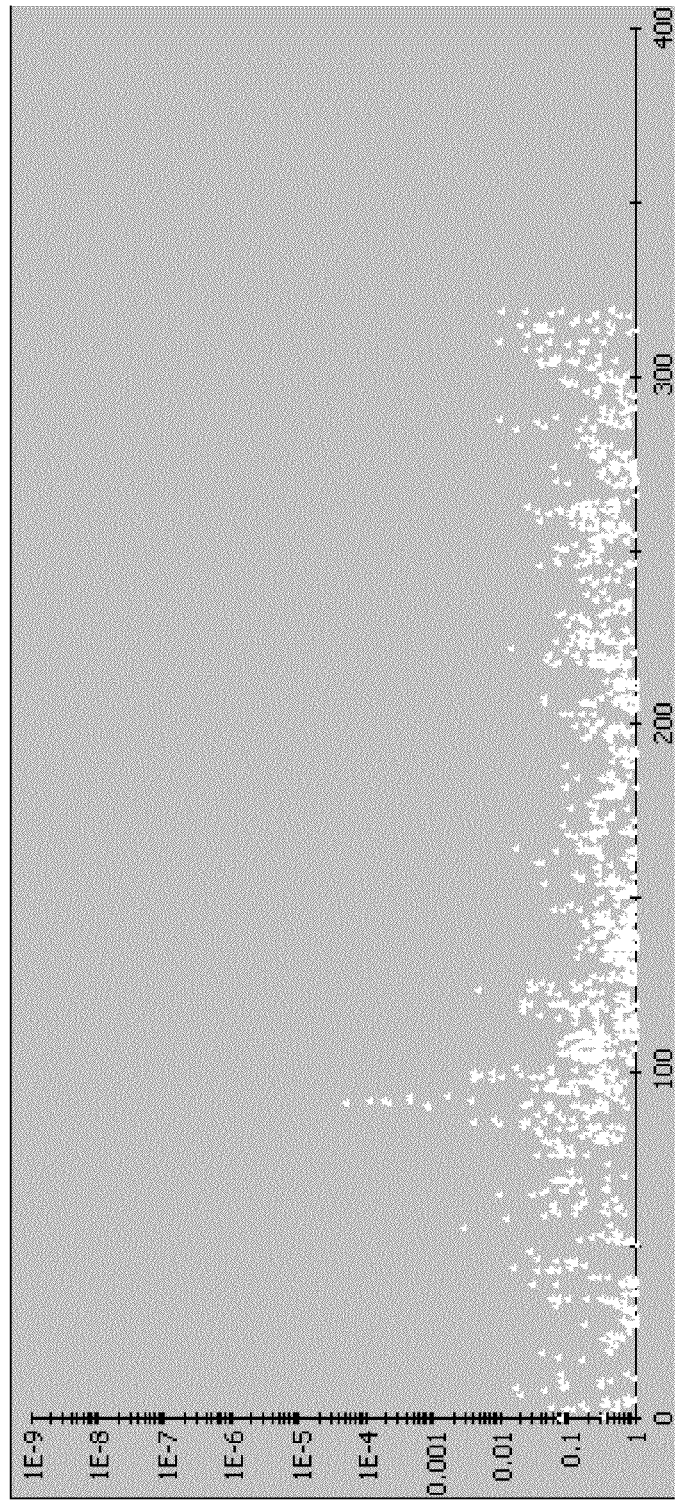
FIG. 2: Associations between marker loci on chromosome 1 and NDF digestibility in a Stiff Stalk subpopulation

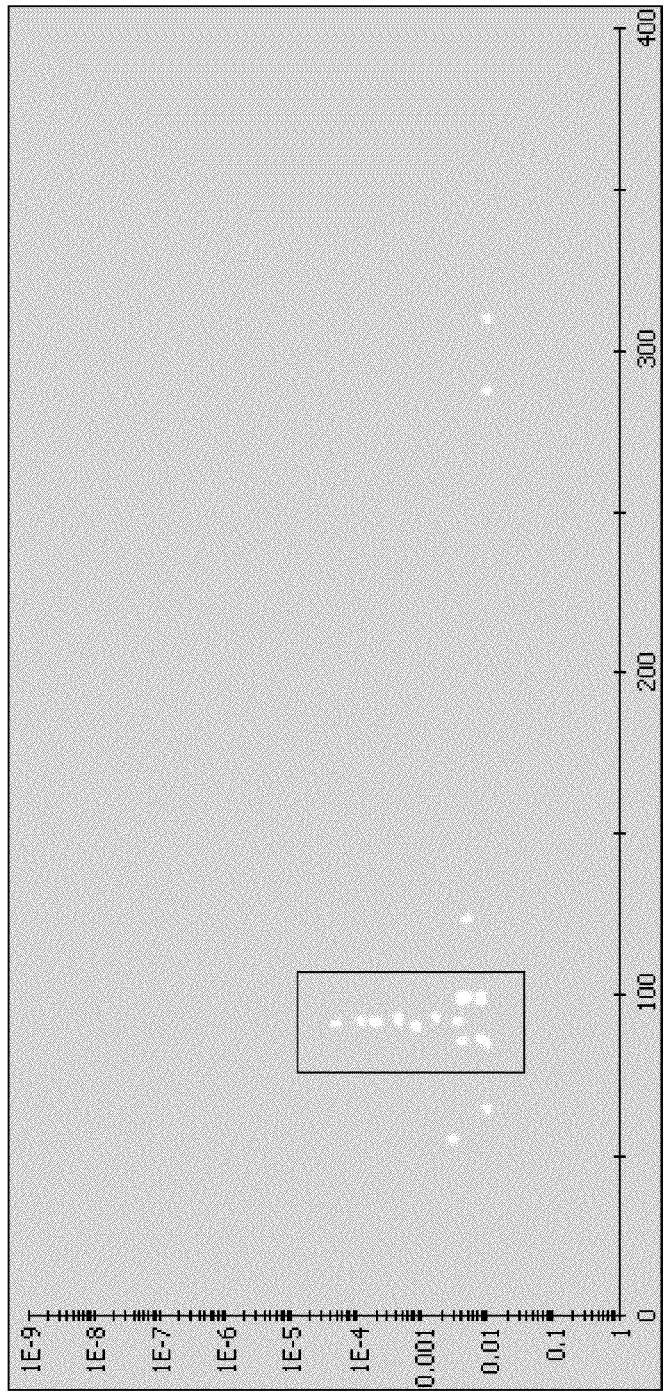
FIG. 3: Associations between marker loci on chromosome 1 and NDF digestibility in a Stiff Stalk subpopulation p ≤ 0.01

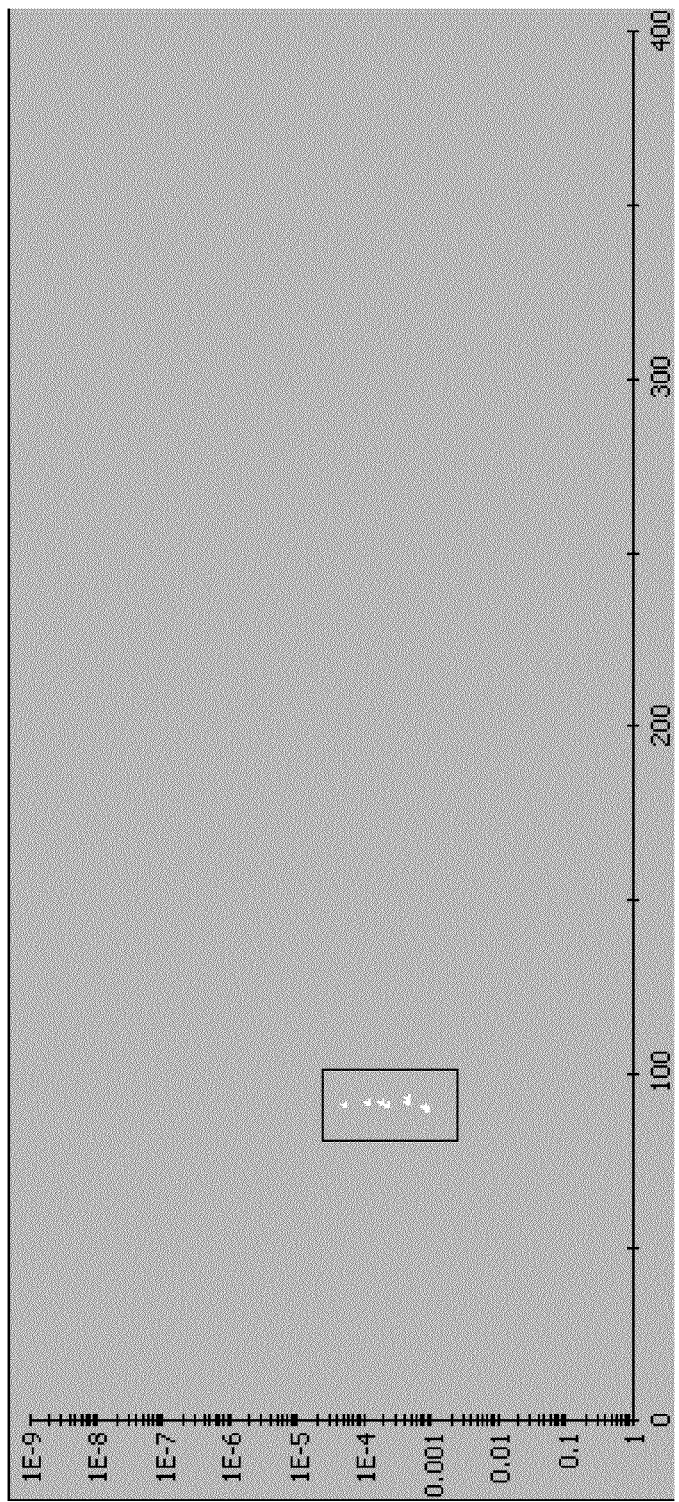
FIG. 4: Associations between marker loci on chromosome 1 and NDF digestibility in a Stiff Stalk subpopulation at p ≤ 0.001.

FIG. 5 Results from candidate gene association study

| Marker | Position in SEQ ID NO:8 | SNP | Present, Absent | mean1, mean2 | P asymptotic | P permutation |
|---|---|---|---|---|---|---|
| SCW_04_5b | 156 | T | (40,11) | (36.8610, 39.5355) | 1.98E-04 | 9.00E-05 |
| SCW_04_5b | 156 | C | (11,40) | (39.5355, 36.8610) | 1.98E-04 | 1.06E-04 |
| SCW_04_5b | 208 | G | (38,13) | (36.7587, 39.4231) | 4.78E-04 | 2.10E-04 |
| SCW_04_5b | 208 | T | (13,38) | (39.4231, 36.7587) | 4.78E-04 | 2.58E-04 |
| SCW_04_5b | 482 | T | (39,12) | (36.7372, 39.7150) | 9.04E-05 | 4.00E-05 |
| SCW_04_5b | 482 | C | (12,39) | (39.7150, 36.7372) | 9.04E-05 | 6.80E-05 |
| SCW_04_5b | 613 | A | (12,39) | (39.7150, 36.7372) | 9.04E-05 | 5.00E-05 |
| SCW_04_5b | 613 | G | (39,12) | (36.7372, 39.7150) | 9.04E-05 | 5.60E-05 |
| SCW_04_5b | 621 | G | (39,12) | (36.7372, 39.7150) | 9.04E-05 | 4.40E-05 |
| SCW_04_5b | 621 | A | (12,39) | (39.7150, 36.7372) | 9.04E-05 | 5.20E-05 |

FIG. 6: PHM Marker Information

| Marker Locus | Reference Sequence (SEQ ID NO:) | | Forward (SEQ ID NO:) | Reverse (SEQ ID NO:) |
|---|---|---|---|---|
| PHM8098 | 1 | Internal | 10 | 11 |
| | | External | 9 | 12 |
| PHM14801 | 2 | Internal | 14 | 15 |
| | | External | 13 | 16 |
| PHM4175 | 3 | Internal | 18 | 19 |
| | | External | 17 | 20 |
| PHM1783 | 4 | Internal | 22 | 23 |
| | | External | 21 | 24 |
| PHM3364 | 5 | Internal | 26 | 27 |
| | | External | 25 | 28 |
| PHM1730 | 6 | Internal | 30 | 31 |
| | | External | 29 | 32 |
| PHM4359 | 7 | Internal | 34 | 35 |
| | | External | 33 | 36 |
| PHM9167 | 8 | Internal | 38 | 39 |
| | | External | 37 | 40 |
| PHM13936 | 94 | Internal | 51 | 52 |
| | | External | 50 | 53 |
| PHM15671 | 95 | Internal | 55 | 56 |
| | | External | 54 | 57 |
| PHM14875 | 96 | Internal | 59 | 60 |
| | | External | 58 | 61 |
| PHM110079 | 97 | Internal | 63 | 64 |
| | | External | 62 | 65 |
| PHM15150 | 98 | Internal | 67 | 68 |
| | | External | 66 | 69 |
| PHM1239 | 99 | Internal | 71 | 72 |
| | | External | 70 | 73 |
| PHM9528 | 100 | Internal | 75 | 76 |
| | | External | 74 | 77 |
| PHM14541 | 101 | Internal | 79 | 80 |
| | | External | 78 | 81 |
| PHM2690 | 102 | Internal | 83 | 84 |
| | | External | 82 | 85 |
| PHM1241 | 103 | Internal | 87 | 88 |
| | | External | 86 | 89 |
| PHM11733 | 104 | Internal | 91 | 92 |
| | | External | 90 | 93 |

SEQUENCE LISTING

```
<160> NUMBER OF SEQ ID NOS: 104

<210> SEQ ID NO 1
<211> LENGTH: 582
<212> TYPE: DNA
<213> ORGANISM: artificial
<220> FEATURE:
<223> OTHER INFORMATION: PHM8098 reference sequence

<400> SEQUENCE: 1
cgagtcagga cgctccgaaa cggaggacac ttgtttataa ccacatcaag tggcggattc      60
caggatgtct atctcttctt tggaataatt gacattctac aagactacga cataaccaag     120
aagctcgagc atgcatacaa gtcctttcag gtcaaccctg gttgcatttc tgccgtagac     180
ccaaagctgt actcgagaag attccaagag ttcagtcgca gagtgttcat cagagaacat     240
taaagaacaa tttgtccagc gggtgactgc tccactggca ttttacatca tgggatccat     300
tggtgaagtc ctggggtatg atggtttcac cgatcccgag cgtgccctgg aacagtggaa     360
aggatggtcg gtttacccga cgcatagttt tctgaataat tggcgtcgag ggaggaggag     420
cactgccgac acgcatgcta atgctgaaag gatgcgagct aaaactgtag agctttgcct     480
tttcaaggac ttgtaaaatg taagtgccgg ctccatgatt gcggagcaca tacccaaacc     540
ttgctgtttg ttatctcttc cgactgaaat ttttttttaat at                       582

<210> SEQ ID NO 2
<211> LENGTH: 836
```

```
<212> TYPE: DNA
<213> ORGANISM: artificial
<220> FEATURE:
<223> OTHER INFORMATION: PHM14801 reference sequence

<400> SEQUENCE: 2
gggatgctta gcccacaatg ggacagttty tgctcttctg actgtgcgtt acttctgcag      60
atacttagga ggcccagaat tggtggaaac cggttactag acatgacaac tcggccacag     120
aagctgacta ggagatgtga agttactgca atacttgtcc tgtatggcct ccccaggtct     180
ggcaatttta tctttatatc tggaggacat cacttttttg tacctacccg gctacccgat     240
tcaaatactg cggttcttct catattctgt gaccggtggt gtcatcgttt gtgtcacaac     300
gctattgcag gctactgaca ggttccatcc tcgcccatga gctgatgcac gggtggctgc     360
gtctcaaagg tacatccgta tatgcatgga tggatggaca aaacatttcg tacaaccatt     420
tatcatcttt atttatttat gaattcgaca gaagaaaaat gtattaggtt ccatcctcgc     480
ccatgagctg atgcacgggt ggctgcgtct caaaggtaca tggatggatg acaaaaacat     540
ttcgtacaac catttatcat ctttatttat gaatttcttg gaaaaaatat atattttttcc    600 gccaaaagct ctaccggatc gtacttttca ttcaggttac cgaaacctaa acgcggaggt     660
ggaagaaggc atatgccagg tcatgtctta cttgtggctg gaatcagaga ttcttccgtc     720
atcctcgagg cacgcgcagg cacagccttc atcatcctat gcctcctcct cgtcgtcgtc     780
ctcctcctcc tcatcctatc cagcaacatc atccgagtgg ggacttgggt aaaaaa        836

<210> SEQ ID NO 3
<211> LENGTH: 556
<212> TYPE: DNA
<213> ORGANISM: artificial
<220> FEATURE:
<223> OTHER INFORMATION: PHM4175 reference sequence

<400> SEQUENCE: 3
aaatcccaat caaaacgcag taatcgggga cggctgcctc atcgggcccg acgtcgcggt      60
cgggccaggc tgcgtggtgg aggccggggt gcgcctgtcc cgctgcaccg tcatgcgcgc     120
cgcgcgcgtc aagcagcacg cctgcgtctc cagcagcatc atcggctggc actccaccgt     180
cggcaagtgg gcgcgcgtcg agaacatgac catcctcggc gaggacgtcc acgtctgcga     240
cgagatctac agcaacggcg cgtcgtgct cccgcacaag gagatcaaat ccagcatcct     300
caagcccgag atcgtcatgt gatccggag taaatctggg gcgccaaatc caaatcacaa     360
ggggcccttg cattgcattg cattgcatcg catcgcatcc catcccatcc cgatatgctt     420
catacttttg ttgtttgatt ttttgctcgg ttgtttgtct gcaagtgtaa ccagttgtcg     480
agtgtttaat ttgtcggcta tatagactat tttcaagttt cgctccgtgc tttagatagt     540
tcgtggtacg ttatgt                                                    556

<210> SEQ ID NO 4
<211> LENGTH: 664
<212> TYPE: DNA
<213> ORGANISM: artificial
<220> FEATURE:
<223> OTHER INFORMATION: PHM1783 reference sequence

<400> SEQUENCE: 4
gacatatatt atatcatctg ttgctggagc gataggtatc tttagtggaa ctatatatgc      60
tatgactaaa ggtaacagcc gtactcaata ctaaacaacc ttctatctct tggtcgtata     120
tgcatgtggc atgtataaac agctaaaatt cttgtttagg tgccattaac cagctaacca     180
```

```
agaatttagc ttgtgaatgg gctaaggaca acataagagc caactctgtc gctccgtggt    240
acatcaccac ttcacttacg gaaggagtaa gaatcttcta ttgtttcata ttaacgactt    300
aagtgtatca tattccctcc attctaaatt ataggttgtt gtgttttttc tagatatata    360
tcttttgcta cacacatgaa tatacattat tctcaataca tctagataca tagtaaaagt    420
tatatattta aaaactagaa tgacttccaa tttgaaatga agtatctcct acattataac    480
cctaatccgt tgtttcctct gactactgct ttcttttgtg aagattttgg caaataagaa    540
ctttgaggaa caagttgtga gtcgaactcc gcttggacgt gtcggagaac ctggagaagt    600
atcggcactt gttgcttttc tttgcatgcc gggttccact tatattagcg gccaaacgat    660 tscg                                                                  664

<210> SEQ ID NO 5
<211> LENGTH: 509
<212> TYPE: DNA
<213> ORGANISM: artificial
<220> FEATURE:
<223> OTHER INFORMATION: PHM3364 reference sequence

<400> SEQUENCE: 5
gagtggtccc agtcacgacg gaccatgtat agtgactaga catggtaggg tggggtggtg     60
tcgtggtgaa gccatcagcc catcactgcc gactggagct ttaaggggta gaggaatcat    120
gcttttattt gctcattctg tctgggtcac tgatgttcag gattaagacc aacttcattc    180
ttggtgttgg gtataggtgt gatgcacact tgtttccttc actatgatgt ttgggatgta    240
gcatcctact gacacgcacg tttatactag gtttcacata gacttgcata tctaagtaat    300
tttgtggtgc tgtgacctac tgacctttta tcttgggttg tgtggagaaa atgtcgtgtt    360
gctttggtta gctgtggtta gtcttttcca gattgctgtt tattgttatc taaattcagt    420
ttatgtagta aatttcatca ggcgctggaa atttctggtg tgatgtcacg ttaactcgct    480
ggtggttcta caaccggaat tttttttatt                                     509

<210> SEQ ID NO 6
<211> LENGTH: 662
<212> TYPE: DNA
<213> ORGANISM: artificial
<220> FEATURE:
<223> OTHER INFORMATION: PHM1730 reference sequence

<400> SEQUENCE: 6
ggtttaaaac atagcaagtc gttttagaac aaccagataa tccgcctgcc ggtatgtcct     60
cttcctccat gcatgtactt tcaccgtttg gatttcctga tactgctgct gtcgcctaca    120
tatgggagct aattctgcat tcttttacct ggcattacga acgtgagctc aattttgatg    180
ctgtagtaat actgtaccca gagcattgt ttcgcttgtt atgtaggcac acatggctga    240
agcgagttcc cgagtgaagg aatgctgccg gcgactcggc cgtgagctga aacggctccc    300
cagcaacgaa gagatcgcgg tggacactgg catgacgatc cggcgggtgg aggcggccat    360
gagcctcccg aaatacagcg tgtccttcac gagcaaggtc gggtgcacgg acgtcacgta    420
ccaggtttgt tcatccttca gtagggaga cgctacatga cactaagaat gacgcctgaa    480
tctgacggcc tccgcttcgc ttcgtcgatc cggcaggaga tcatgccgga cacgagcgcc    540
gagacggcgg aggaaacgct gcaccggtgg ctgatgaaaa aggacttaac acggcgctgg    600
acagcctgag cccgcgccaa aaacagttat ccggtaccgg ttcgcatcta tggccggccg    660
gc                                                                   662
```

<210> SEQ ID NO 7
<211> LENGTH: 625
<212> TYPE: DNA
<213> ORGANISM: artificial
<220> FEATURE:
<223> OTHER INFORMATION: PHM4359 reference sequence

<400> SEQUENCE: 7

```
tgtttgggga atgcggtgct gggtaagttt gggttgttct atatctatca taagccaaaa      60
cagcatcccg tgtcaagtac gaatttgttg atgtcttgcc ctatatgata tgaacttcta     120
aattgccgta taaaatttac tgcaaacctc aacgcaggtg aagaatcatc ctattaagga     180
acagccacgt gactcacctg gcacggtgat cctttcaaaa tcgccaaagc tagaagtatg     240
ttgtctataa tatattgggg cctacaacgt tcattatatg ttttctttat gcaggctgca     300
aacgatatat tgtttaatta attaataatt tttgtgtgtg tgttttcata ggcaaatttt     360
tcaagagcag ttgctgccct cagcaaggct cagacaaata agattaaacg attccttcca     420
aaccccgaac ggcactgggg tccgaaggtc agagcaggcc ggaaaatcac gagcaaacat     480
gtctctctgt tgggccctga cgctatcaag ggtgctgtga acggtggtga ctgccaaaaa     540
kaaggaaacg gtgctgagcc aaatagtaca gcctcaaaac ccgaggggat caaaacttta     600
ggataccctc aaaaaaaccc caaaa                                           625
```

<210> SEQ ID NO 8
<211> LENGTH: 600
<212> TYPE: DNA
<213> ORGANISM: artificial
<220> FEATURE:
<223> OTHER INFORMATION: PHM9167 reference sequence

<400> SEQUENCE: 8

```
tcaggacgag atcttggaaa tcgccgacca atttgcccgg tccggaccg ccgacgagct       60 gcccaagacc cccgtgctgt gcaagcccaa cgtggacgcc atggaggagg cgctcaggat     120
cgccaacgtc aacccgcaca aggcggtgag tttccgagct ctggcaccca acacaatttc     180
cattcctgtt cctgacgtcg catccacacc ttgaagaaac atttttttatt attttttatt     240 ctgcttgacc atcttctccc tgacgaaagc tttacctgat tgatctcctg cagatcttct     300
tcgacgacag cgtacgcaac atccaggccg ggaagcagat tggcctccac acggtgctgg     360
tgggcaaatc gcagcgggtg aaaggcgcgg accacgcgct ggagagcatc cacaacatca     420
gggaagcgct gccggagctg tgggaggagg ccgagaaggc ggaggacgtg ctctaccccg     480
aacgcgttgc gatggagacc tcggtcaccg cgtaaaaccc ctgaatgcct ccggtgcacc     540
gtcagccgaa ctttctcgac atctccagac cgcatcaaca tcacatactt tcagtaaata     600
```

<210> SEQ ID NO 9
<211> LENGTH: 20
<212> TYPE: DNA
<213> ORGANISM: artificial
<220> FEATURE:
<223> OTHER INFORMATION: PHM8098 forward external primer

<400> SEQUENCE: 9

```
gtcgaagaga gtcctggata                                                  20
```

<210> SEQ ID NO 10
<211> LENGTH: 21
<212> TYPE: DNA
<213> ORGANISM: artificial

```
<220> FEATURE:
<223> OTHER INFORMATION: PHM8098 forward internal primer

<400> SEQUENCE: 10
ctcctaaacg aaagacactt g                                              21

<210> SEQ ID NO 11
<211> LENGTH: 21
<212> TYPE: DNA
<213> ORGANISM: artificial
<220> FEATURE:
<223> OTHER INFORMATION: PHM8098 reverse internal primer

<400> SEQUENCE: 11
atgcgagtgc ggaagaagaa t                                              21

<210> SEQ ID NO 12
<211> LENGTH: 22
<212> TYPE: DNA
<213> ORGANISM: artificial
<220> FEATURE:
<223> OTHER INFORMATION: PHM8098 reverse external primer

<400> SEQUENCE: 12
tccatctact agtgtacaca ct                                             22

<210> SEQ ID NO 13
<211> LENGTH: 19
<212> TYPE: DNA
<213> ORGANISM: artificial
<220> FEATURE:
<223> OTHER INFORMATION: PHM14801 forward external primer

<400> SEQUENCE: 13
tcaacgaagc catggaagg                                                 19

<210> SEQ ID NO 14
<211> LENGTH: 20
<212> TYPE: DNA
<213> ORGANISM: artificial
<220> FEATURE:
<223> OTHER INFORMATION: PHM14801 forward internal primer

<400> SEQUENCE: 14
acgccacatg cctgagacta                                                20

<210> SEQ ID NO 15
<211> LENGTH: 21
<212> TYPE: DNA
<213> ORGANISM: artificial
<220> FEATURE:
<223> OTHER INFORMATION: PHM14801 reverse internal primer

<400> SEQUENCE: 15
ccacctttct cggatgatgt t                                              21

<210> SEQ ID NO 16
<211> LENGTH: 20
<212> TYPE: DNA
<213> ORGANISM: artificial
<220> FEATURE:
<223> OTHER INFORMATION: PHM14801 reverse external primer

<400> SEQUENCE: 16
gcttcttccc ggtatgagat                                                20
```

```
<210> SEQ ID NO 17
<211> LENGTH: 18
<212> TYPE: DNA
<213> ORGANISM: artificial
<220> FEATURE:
<223> OTHER INFORMATION: PHM4175 forward external primer

<400> SEQUENCE: 17
gaaggcgccc gccaggct                                                 18

<210> SEQ ID NO 18
<211> LENGTH: 18
<212> TYPE: DNA
<213> ORGANISM: artificial
<220> FEATURE:
<223> OTHER INFORMATION: PHM4175 forward internal primer

<400> SEQUENCE: 18
cggtcatcgg ggacggct                                                 18

<210> SEQ ID NO 19
<211> LENGTH: 21
<212> TYPE: DNA
<213> ORGANISM: artificial
<220> FEATURE:
<223> OTHER INFORMATION: PHM4175 reverse internal primer

<400> SEQUENCE: 19
agacgactga tacctatcta c                                             21

<210> SEQ ID NO 20
<211> LENGTH: 22
<212> TYPE: DNA
<213> ORGANISM: artificial
<220> FEATURE:
<223> OTHER INFORMATION: PHM4175 reverse external primer

<400> SEQUENCE: 20
gtagtatacg aagagaagtt gt                                            22

<210> SEQ ID NO 21
<211> LENGTH: 22
<212> TYPE: DNA
<213> ORGANISM: artificial
<220> FEATURE:
<223> OTHER INFORMATION: PHM1783 forward external primer

<400> SEQUENCE: 21
tcgtttctga tggctactaa tc                                            22

<210> SEQ ID NO 22
<211> LENGTH: 22
<212> TYPE: DNA
<213> ORGANISM: artificial
<220> FEATURE:
<223> OTHER INFORMATION: PHM1783 forward internal primer

<400> SEQUENCE: 22
gtcaggcagc attatattca ta                                            22

<210> SEQ ID NO 23
<211> LENGTH: 20
<212> TYPE: DNA
<213> ORGANISM: artificial
<220> FEATURE:
<223> OTHER INFORMATION: PHM1783 reverse internal primer

<400> SEQUENCE: 23
```

```
gttcacagtc atacctccgt                                              20

<210> SEQ ID NO 24
<211> LENGTH: 21
<212> TYPE: DNA
<213> ORGANISM: artificial
<220> FEATURE:
<223> OTHER INFORMATION: PHM1783 reverse external primer

<400> SEQUENCE: 24
acaacagcta ttgtcgtttc c                                            21

<210> SEQ ID NO 25
<211> LENGTH: 22
<212> TYPE: DNA
<213> ORGANISM: artificial
<220> FEATURE:
<223> OTHER INFORMATION: PHM3364 forward external primer

<400> SEQUENCE: 25
agaagcatta ggctattact ac                                           22

<210> SEQ ID NO 26
<211> LENGTH: 22
<212> TYPE: DNA
<213> ORGANISM: artificial
<220> FEATURE:
<223> OTHER INFORMATION: PHM3364 forward internal primer

<400> SEQUENCE: 26
gaccatgtat agtgactaga ca                                           22

<210> SEQ ID NO 27
<211> LENGTH: 21
<212> TYPE: DNA
<213> ORGANISM: artificial
<220> FEATURE:
<223> OTHER INFORMATION: PHM3364 reverse internal primer

<400> SEQUENCE: 27
ttctggttag aacaccaccc a                                            21

<210> SEQ ID NO 28
<211> LENGTH: 22
<212> TYPE: DNA
<213> ORGANISM: artificial
<220> FEATURE:
<223> OTHER INFORMATION: PHM3364 reverse external primer

<400> SEQUENCE: 28
tgtcattcag actcagttcc aa                                           22

<210> SEQ ID NO 29
<211> LENGTH: 22
<212> TYPE: DNA
<213> ORGANISM: artificial
<220> FEATURE:
<223> OTHER INFORMATION: PHM1730 forward external primer

<400> SEQUENCE: 29
tttagattct ccacttactc tc                                           22

<210> SEQ ID NO 30
<211> LENGTH: 22
<212> TYPE: DNA
<213> ORGANISM: artificial
```

```
<220> FEATURE:
<223> OTHER INFORMATION: PHM1730 forward internal primer

<400> SEQUENCE: 30
ctggtggatc aaacaagcaa ta                                        22

<210> SEQ ID NO 31
<211> LENGTH: 19
<212> TYPE: DNA
<213> ORGANISM: artificial
<220> FEATURE:
<223> OTHER INFORMATION: PHM1730 reverse internal primer

<400> SEQUENCE: 31
gatgtcgtgc agggtcctg                                            19

<210> SEQ ID NO 32
<211> LENGTH: 18
<212> TYPE: DNA
<213> ORGANISM: artificial
<220> FEATURE:
<223> OTHER INFORMATION: PHM1730 reverse external primer

<400> SEQUENCE: 32
ttccggaacg cgcccagc                                             18

<210> SEQ ID NO 33
<211> LENGTH: 19
<212> TYPE: DNA
<213> ORGANISM: artificial
<220> FEATURE:
<223> OTHER INFORMATION: PHM4359 forward external primer

<400> SEQUENCE: 33
tcggatctca agcacccat                                            19

<210> SEQ ID NO 34
<211> LENGTH: 21
<212> TYPE: DNA
<213> ORGANISM: artificial
<220> FEATURE:
<223> OTHER INFORMATION: PHM4359 forward internal primer

<400> SEQUENCE: 34
atgttatttg ggacatcatg c                                         21

<210> SEQ ID NO 35
<211> LENGTH: 21
<212> TYPE: DNA
<213> ORGANISM: artificial
<220> FEATURE:
<223> OTHER INFORMATION: PHM4359 reverse internal primer

<400> SEQUENCE: 35
aaagcacagg cacaacacaa t                                         21

<210> SEQ ID NO 36
<211> LENGTH: 21
<212> TYPE: DNA
<213> ORGANISM: artificial
<220> FEATURE:
<223> OTHER INFORMATION: PHM4359 reverse external primer

<400> SEQUENCE: 36
tttgttcgtt caaaatccaa c                                         21
```

-continued

<210> SEQ ID NO 37
<211> LENGTH: 18
<212> TYPE: DNA
<213> ORGANISM: artificial
<220> FEATURE:
<223> OTHER INFORMATION: PHM9167 forward external primer

<400> SEQUENCE: 37
cgtgagagcc ctcaagag                                                    18

<210> SEQ ID NO 38
<211> LENGTH: 19
<212> TYPE: DNA
<213> ORGANISM: artificial
<220> FEATURE:
<223> OTHER INFORMATION: PHM9167 forward internal primer

<400> SEQUENCE: 38
agatcttcga catcgccga                                                   19

<210> SEQ ID NO 39
<211> LENGTH: 20
<212> TYPE: DNA
<213> ORGANISM: artificial
<220> FEATURE:
<223> OTHER INFORMATION: PHM9167 reverse internal primer

<400> SEQUENCE: 39
gacatgtgat cgttgatgcg                                                  20

<210> SEQ ID NO 40
<211> LENGTH: 22
<212> TYPE: DNA
<213> ORGANISM: artificial
<220> FEATURE:
<223> OTHER INFORMATION: PHM9167 reverse external primer

<400> SEQUENCE: 40
ccaaacatga tctcatctgt tc                                               22

<210> SEQ ID NO 41
<211> LENGTH: 1734
<212> TYPE: DNA
<213> ORGANISM: Zea mays

<400> SEQUENCE: 41
atgggggcgg cggcgccatc gtcgtggctt attgcgttca tcctgttctt cggcacgttg      60
gtagcgttgc cgcagtcgtc acacggcggc ggcacaacca gacactacac cttcaacgtg     120
acgatgaaga aggtgacgcg gctgtgcacc acccgcgcca tcccgacggt gaacggccag     180
ttccccggcc ccaagatagt caccagggag ggcgaccgcg tcgtcgtcaa ggtgctgaac     240
aatgtcaagg acaacgttac catccactgg cacggcgttc ggcagctgcg cacggggtgg     300
tcggacgggc cagcgtacgt gacgcagtgc cccatccaga cggggcagag cttcgtgtac     360
aacttcacca tcacggggca gcggggcacc ctgttctggc acgcgcacgt ctcctggatg     420
cgcgccacgc tctacgggcc catcgtcatc ctccccaagc gcggcgtgcc atacccgctc     480
ccggttaaac cctacaagga cgtcccagtc atcttcggag agtggttcaa cgcggatcca     540
gagacaattg tcgcccaggc gcttcagact ggagcaggcc caaacgtgtc ggacgccttc     600
accatcaacg ggctcccggg ccctttgtac aactgctcca gcaaagacac gttcaagctg     660
aaggtgctgc ccggcaaatg gtacctgctc cgtctcatca acgctgcgct caacgacgag     720
ctcttcttct ccgtcgccaa ccacacgctc accgtcgtcg acgtcgacgc cgcctacgtc     780

```
aagccgttcc gcacggacat cgtgctcatc acgccgggcc agaccaccaa cgtgctcctg    840
cgcgccgagc ccgacgcggg gtgccccgcg gccacgcacc tcatgctggc gcgcccctac    900
ggcacgggcc agccgggcac cttcgacaac accaccgtcg ccgccgtgct cgagtacgcg    960
ccgccgggcc acatcaggag cctcccgctc ttccggccct cgctcccgc gctcaacgac    1020 acggccttcg ccgcgaacta cagcgccagg ctccggagcc tggccacccc ggactacccg    1080
gccaacgtgc cccgcgccgt ggaccgctcc ttcttcttcg ccgtcgggct cggcaccaac    1140
ccctgccccg tcaaccagac gtgccagggg cccaacggga ccatgttcac ggcgtccatg    1200
aacaacgtgt ccttcaacat gcccaccacc gcgctcctgc aggcgcacta cggcagcgtc    1260
gccggcgtgt acgcccccga cttccccgtc gcgccgctcg agccgttcaa ctacactggc    1320
acgccgccga caacaccaa cgtctcccac gggaccaagg tggtggtgct ggactacaat    1380
accagcgtcg aggtggtgct gcaggccacc agcatcctcg gcgccgagag ccacccgctg    1440
cacctccacg gattcgactt cttcgtcgtc ggccaaggct tcggcaacta cgactcgtcc    1500
aaggacccac ccaagtttaa cctagtcgac ccggtgcaaa ggaacaccgt cggcgtgccg    1560
gcagggggct gggtcgccat caggttcttc gcggataatc ccggtgtttg gttcatgcat    1620
tgccatctgg aggtgcacac aagctggggg ttgaagatgg catgggtggt caacgatggc    1680
ccgttgcctg agcagaagct gatgccgccg ccggccgatc ttcccaagtg ctga          1734
```

<210> SEQ ID NO 42
<211> LENGTH: 577
<212> TYPE: PRT
<213> ORGANISM: Zea mays

<400> SEQUENCE: 42

```
Met Gly Ala Ala Ala Pro Ser Ser Trp Leu Ile Ala Phe Ile Leu Phe
1               5                   10                  15

Phe Gly Thr Leu Val Ala Leu Pro Gln Ser Ser His Gly Gly Gly Thr
            20                  25                  30

Thr Arg His Tyr Thr Phe Asn Val Thr Met Lys Lys Val Thr Arg Leu
        35                  40                  45

Cys Thr Thr Arg Ala Ile Pro Thr Val Asn Gly Gln Phe Pro Gly Pro
    50                  55                  60

Lys Ile Val Thr Arg Glu Gly Asp Arg Val Val Val Lys Val Leu Asn
65                  70                  75                  80

Asn Val Lys Asp Asn Val Thr Ile His Trp His Gly Val Arg Gln Leu
                85                  90                  95

Arg Thr Gly Trp Ser Asp Gly Pro Ala Tyr Val Thr Gln Cys Pro Ile
            100                 105                 110

Gln Thr Gly Gln Ser Phe Val Tyr Asn Phe Thr Ile Thr Gly Gln Arg
        115                 120                 125

Gly Thr Leu Phe Trp His Ala His Val Ser Trp Met Arg Ala Thr Leu
    130                 135                 140

Tyr Gly Ala Ile Val Ile Leu Pro Lys Arg Gly Val Pro Tyr Pro Leu
145                 150                 155                 160

Pro Val Lys Pro Tyr Lys Asp Val Pro Val Ile Phe Gly Glu Trp Phe
                165                 170                 175

Asn Ala Asp Pro Glu Thr Ile Val Ala Gln Ala Leu Gln Thr Gly Ala
            180                 185                 190

Gly Pro Asn Val Ser Asp Ala Phe Thr Ile Asn Gly Leu Pro Gly Pro
        195                 200                 205
```

```
Leu Tyr Asn Cys Ser Ser Lys Asp Thr Phe Lys Leu Lys Val Leu Pro
            210                 215                 220

Gly Lys Trp Tyr Leu Leu Arg Leu Ile Asn Ala Ala Leu Asn Asp Glu
225                 230                 235                 240

Leu Phe Phe Ser Val Ala Asn His Thr Leu Thr Val Val Asp Val Asp
                245                 250                 255

Ala Ala Tyr Val Lys Pro Phe Arg Thr Asp Ile Val Leu Ile Thr Pro
            260                 265                 270

Gly Gln Thr Thr Asn Val Leu Leu Arg Ala Glu Pro Asp Ala Gly Cys
            275                 280                 285

Pro Ala Ala Thr His Leu Met Leu Ala Arg Pro Tyr Gly Thr Gly Gln
290                 295                 300

Pro Gly Thr Phe Asp Asn Thr Thr Val Ala Ala Val Leu Glu Tyr Ala
305                 310                 315                 320

Pro Pro Gly His Ile Arg Ser Leu Pro Leu Phe Arg Pro Ser Leu Pro
            325                 330                 335

Ala Leu Asn Asp Thr Ala Phe Ala Ala Asn Tyr Ser Ala Arg Leu Arg
            340                 345                 350

Ser Leu Ala Thr Pro Asp Tyr Pro Ala Asn Val Pro Arg Ala Val Asp
            355                 360                 365

Arg Ser Phe Phe Phe Ala Val Gly Leu Gly Thr Asn Pro Cys Pro Val
370                 375                 380

Asn Gln Thr Cys Gln Gly Pro Asn Gly Thr Met Phe Thr Ala Ser Met
385                 390                 395                 400

Asn Asn Val Ser Phe Asn Met Pro Thr Thr Ala Leu Leu Gln Ala His
                405                 410                 415

Tyr Gly Ser Val Ala Gly Val Tyr Thr Pro Asp Phe Pro Val Ala Pro
            420                 425                 430

Leu Glu Pro Phe Asn Tyr Thr Gly Thr Pro Asn Asn Thr Asn Val
            435                 440                 445

Ser His Gly Thr Lys Val Val Leu Asp Tyr Asn Thr Ser Val Glu
            450                 455                 460

Val Val Leu Gln Ala Thr Ser Ile Leu Gly Ala Glu Ser His Pro Leu
465                 470                 475                 480

His Leu His Gly Phe Asp Phe Val Val Gly Gln Gly Phe Gly Asn
                485                 490                 495

Tyr Asp Ser Ser Lys Asp Pro Pro Lys Phe Asn Leu Val Asp Pro Val
            500                 505                 510

Gln Arg Asn Thr Val Gly Val Pro Ala Gly Gly Trp Val Ala Ile Arg
            515                 520                 525

Phe Phe Ala Asp Asn Pro Gly Val Trp Phe Met His Cys His Leu Glu
530                 535                 540

Val His Thr Ser Trp Gly Leu Lys Met Ala Trp Val Val Asn Asp Gly
545                 550                 555                 560

Pro Leu Pro Glu Gln Lys Leu Met Pro Pro Ala Asp Leu Pro Lys
            565                 570                 575

Cys

<210> SEQ ID NO 43
<211> LENGTH: 1967
<212> TYPE: DNA
<213> ORGANISM: Zea mays

<400> SEQUENCE: 43
cggccggcca tataacaa tcgtcctcga tctctcggcc gagatcgatc tgcgtgtgcc    60
```

```
aagggagatg ggggcggcgg cgccatcgtc gtggcttatt gcgttcatcc tgttcttcgg    120
cacgttggta gcgttgccgc agtcgtcaca cggcggcggc acaaccagac actacacctt    180
caacgtgacg atgaagaagg tgacgcggct gtgcaccacc cgcgccatcc cgacggtgaa    240
cggccagttc cccggcccca agatagtcac cagggagggc gaccgcgtcg tcgtcaaggt    300
gctgaacaat gtcaaggaca acgttaccat ccactggcac ggcgttcggc agctgcgcac    360
ggggtggtcg gacgggccag cgtacgtgac gcagtgcccc atccagacgg ggcagagctt    420
cgtgtacaac ttcaccatca cggggcagcg gggcaccctg ttctggcacg cgcacgtctc    480
ctggatgcgc gccacgctct acggggccat cgtcatcctc cccaagcgcg cgtgccata    540 cccgctcccg gttaaaccct caaggacgt cccagtcatc ttcggagagt ggttcaacgc    600
ggatccagag acaattgtcg cccaggcgct tcagactgga gcaggccaa acgtgtcgga    660 cgccttcacc atcaacgggc tcccgggcc tttgtacaac tgctccagca agacacgtt    720 caagctgaag gtgctgcccg gcaaatggta cctgctccgt ctcatcaacg ctgcgctcaa    780
cgacgagctc ttcttctccg tcgccaacca cactcacc gtcgtcgacg tcgacgccgc    840
ctacgtcaag ccgttccgca cggacatcgt gctcatcacg ccgggccaga ccaccaacgt    900
gctcctgcgc gccgagcccg acgcggggtg ccccgcggcc acgcacctca tgctggcgcg    960
cccctacggc acgggccagc cgggcacctt cgacaacacc accgtcgccg ccgtgctcga    1020
gtacgcgccg ccgggccaca tcaggagcct cccgctcttc cggccctcgc tccccgcgct    1080
caacgacacg gccttcgccg cgaactacag cgccaggctc cggagcctgg ccaccccgga    1140
ctacccggcc aacgtgcccc gcgccgtgga ccgctccttc ttcttcgccg tcgggctcgg    1200
caccaacccc tgccccgtca accagacgtg ccaggggccc aacgggacca tgttcacggc    1260
gtccatgaac aacgtgtcct tcaacatgcc caccaccgcg ctcctgcagg cgcactacgg    1320
cagcgtcgcc ggcgtgtaca cgcccgactt ccccgtcgcg ccgctcgagc cgttcaacta    1380
cactggcacg ccgccgaaca acaccaacgt ctcccacggg accaaggtgg tggtgctgga    1440
ctacaatacc agcgtcgagg tggtgctgca ggccaccagc atcctcggcg ccgagagcca    1500
cccgctgcac ctccacggat cgacttctt cgtcgtcggc caaggcttcg gcaactacga    1560
ctcgtccaag gacccaccca gtttaacct agtcgaccg gtgcaaagga acaccgtcgg    1620
cgtgccggca gggggctggg tcgccatcag gttcttcgcg gataatcccg gtgtttggtt    1680
catgcattgc catctggagg tgcacacaag ctgggggttg aagatggcat gggtggtcaa    1740
cgatggcccg ttgcctgagc agaagctgat gccgccgccg gccgatcttc ccaagtgctg    1800
aagatccacc gcgcgttgac attgtccaac attatgattc gtttctattg cataaacata    1860
tcaatggaga tacacattgt cgtcgtacat atagcgtcgt acacagcgtt taaagaggct    1920
ttgtggtttc tctatgcaaa aaaaaaaaaa aaaaaaaaaa aaaaaaa             1967
```

<210> SEQ ID NO 44
<211> LENGTH: 576
<212> TYPE: PRT
<213> ORGANISM: Zea mays

<400> SEQUENCE: 44

Met Gly Ala Ala Pro Ser Ser Trp Leu Ala Phe Ile Leu Phe Phe
1               5                   10                  15

Gly Thr Leu Val Ala Leu Pro Gln Ser Ser His Gly Gly Thr Thr
                20                  25                  30

Arg His Tyr Thr Phe Asn Val Thr Met Lys Lys Val Thr Arg Leu Cys

-continued

```
                35                  40                  45
Thr Thr Arg Ala Ile Pro Thr Val Asn Gly Gln Phe Pro Gly Pro Lys
 50                  55                  60
Ile Val Thr Arg Glu Gly Asp Arg Val Val Lys Val Leu Asn Asn
 65                  70                  75                  80
Val Lys Asp Asn Val Thr Ile His Trp His Gly Val Arg Gln Leu Arg
                 85                  90                  95
Thr Gly Trp Ser Asp Gly Pro Ala Tyr Val Thr Gln Cys Pro Ile Gln
                100                 105                 110
Thr Gly Gln Ser Phe Val Tyr Asn Phe Thr Ile Thr Gly Gln Arg Gly
                115                 120                 125
Thr Leu Phe Trp His Ala His Val Ser Trp Met Arg Ala Thr Leu Tyr
                130                 135                 140
Gly Ala Ile Val Ile Leu Pro Lys Arg Gly Val Pro Tyr Pro Leu Pro
145                 150                 155                 160
Val Lys Pro Tyr Lys Asp Val Pro Val Ile Phe Gly Glu Trp Phe Asn
                165                 170                 175
Ala Asp Pro Glu Thr Ile Val Ala Gln Ala Leu Gln Thr Gly Ala Gly
                180                 185                 190
Pro Asn Val Ser Asp Ala Phe Thr Ile Asn Gly Leu Pro Gly Pro Leu
                195                 200                 205
Tyr Asn Cys Ser Ser Lys Asp Thr Phe Lys Leu Lys Val Leu Pro Gly
                210                 215                 220
Lys Trp Tyr Leu Leu Arg Leu Ile Asn Ala Ala Leu Asn Asp Glu Leu
225                 230                 235                 240
Phe Phe Ser Ile Ala Asn His Thr Leu Thr Val Val Asp Val Asp Ala
                245                 250                 255
Ala Tyr Val Lys Pro Phe Arg Thr Asp Ile Val Leu Ile Thr Pro Gly
                260                 265                 270
Gln Thr Thr Asn Val Leu Leu Arg Ala Glu Pro Asp Ala Gly Cys Pro
                275                 280                 285
Ala Ala Thr His Leu Met Leu Ala Arg Pro Tyr Gly Thr Gly Gln Pro
                290                 295                 300
Gly Thr Phe Asp Asn Thr Thr Val Ala Ala Val Leu Glu Tyr Ala Pro
305                 310                 315                 320
Pro Gly His Ile Arg Ser Leu Pro Leu Phe Arg Pro Ser Leu Pro Ala
                325                 330                 335
Leu Asn Asp Thr Ala Phe Ala Ala Asn Tyr Ser Ala Arg Leu Arg Ser
                340                 345                 350
Leu Ala Thr Pro Asp Tyr Pro Ala Asn Val Pro Arg Ala Val Asp Arg
                355                 360                 365
Ser Phe Phe Phe Ala Val Gly Leu Gly Thr Asn Pro Cys Pro Val Asn
                370                 375                 380
Gln Thr Cys Gln Gly Pro Asn Gly Thr Met Phe Thr Ala Ser Met Asn
385                 390                 395                 400
Asn Val Ser Phe Asn Met Pro Thr Thr Ala Leu Leu Gln Ala His Tyr
                405                 410                 415
Gly Ser Val Ala Gly Val Tyr Thr Pro Asp Phe Pro Val Ala Pro Leu
                420                 425                 430
Glu Pro Phe Asn Tyr Thr Gly Thr Pro Pro Asn Asn Thr Asn Val Ser
                435                 440                 445
His Gly Thr Lys Val Val Val Leu Asp Tyr Asn Thr Ser Val Glu Val
450                 455                 460
```

```
Val Leu Gln Ala Thr Ser Ile Leu Gly Ala Glu Ser His Pro Leu His
465                 470                 475                 480

Leu His Gly Phe Asp Phe Phe Val Val Gly Gln Gly Phe Gly Asn Tyr
                485                 490                 495

Asp Ser Ser Lys Asp Pro Pro Lys Phe Asn Leu Val Asp Pro Val Gln
            500                 505                 510

Arg Asn Thr Val Gly Val Pro Ala Gly Gly Trp Val Ala Ile Arg Phe
            515                 520                 525

Phe Ala Asp Asn Pro Gly Val Trp Phe Met His Cys His Leu Glu Val
            530                 535                 540

His Thr Ser Trp Gly Leu Lys Met Ala Trp Val Val Asn Asp Gly Pro
545                 550                 555                 560

Leu Pro Glu Gln Lys Leu Met Pro Pro Ala Asp Leu Pro Lys Cys
                565                 570                 575

<210> SEQ ID NO 45
<211> LENGTH: 578
<212> TYPE: PRT
<213> ORGANISM: Oryza sativa

<400> SEQUENCE: 45

Met Gly Ala Arg Cys Leu Ala Leu Leu Leu Tyr Gly Thr Leu Leu
1               5                   10                  15

Leu Leu Leu Leu Leu Pro Gln Leu Pro Leu Ala Gly Ala Ala Thr Arg
                20                  25                  30

Tyr Tyr Thr Phe Asn Val Lys Leu Gln Asn Val Thr Arg Leu Cys Asn
                35                  40                  45

Thr Arg Ala Ile Pro Thr Val Asn Gly Lys Phe Pro Gly Pro Lys Ile
50                  55                  60

Val Thr Arg Glu Gly Asp Arg Val Val Val Lys Val Val Asn Asn Ile
65                  70                  75                  80

Lys Asp Asn Ile Thr Ile His Trp His Gly Val Arg Gln Met Arg Thr
                85                  90                  95

Gly Trp Ser Asp Gly Pro Ala Tyr Val Thr Gln Cys Pro Ile Gln Thr
                100                 105                 110

Gly Gln Ser Tyr Val Tyr Asn Phe Thr Ile Asn Gly Gln Arg Gly Thr
            115                 120                 125

Leu Phe Trp His Ala His Val Ser Trp Leu Arg Ser Thr Leu Tyr Gly
            130                 135                 140

Pro Ile Ile Ile Leu Pro Lys Ala Gly Leu Pro Leu Pro Phe Thr Glu
145                 150                 155                 160

Pro His Lys Asp Val Pro Ile Ile Phe Gly Glu Trp Phe Asn Ala Asp
                165                 170                 175

Pro Glu Ala Ile Val Ala Gln Ala Leu Gln Thr Gly Gly Pro Asn
            180                 185                 190

Val Ser Asp Ala Tyr Thr Ile Asn Gly Leu Pro Gly Pro Leu Tyr Asn
            195                 200                 205

Cys Ser Ser Lys Asp Thr Phe Arg Leu Lys Val Gln Pro Gly Lys Met
210                 215                 220

Tyr Leu Leu Arg Leu Ile Asn Ala Ala Leu Asn Asp Glu Leu Phe Phe
225                 230                 235                 240

Ser Val Ala Asn His Thr Leu Thr Val Val Asp Val Asp Ala Ser Tyr
                245                 250                 255

Val Lys Pro Phe Asp Thr Asp Val Leu Ile Thr Pro Gly Gln Thr
                260                 265                 270
```

```
        Thr Asn Val Leu Leu Arg Ala Lys Pro Thr Ala Glu Ala Ala Gly Ala
                275                 280                 285

Thr His Leu Met Met Ala Arg Pro Tyr Ala Thr Gly Arg Pro Gly Thr
            290                 295                 300

Tyr Asp Asn Thr Thr Val Ala Ala Val Leu Glu Tyr Ala Pro Pro Gly
        305                 310                 315                 320

His Ile Lys Ser Leu Pro Leu Leu Arg Pro Ser Leu Pro Ala Leu Asn
                        325                 330                 335

Asp Thr Ala Phe Ala Ala Gly Phe Ala Ala Lys Leu Arg Ser Leu Ala
                            340                 345                 350

Cys Pro Asp Tyr Pro Ser Asn Val Pro Arg Arg Val Asp Lys Pro Phe
                                355                 360                 365

Phe Phe Ala Val Gly Leu Gly Thr Thr Pro Cys Pro Gly Ser Asn Asn
                370                 375                 380

Gln Thr Cys Gln Gly Pro Thr Asn Thr Thr Lys Phe Thr Ala Ser Ile
        385                 390                 395                 400

Asn Asn Val Ser Phe Asp Met Pro Thr Thr Ala Leu Leu Gln Ala His
                        405                 410                 415

Tyr Thr Gly Gln Ser Ala Gly Val Tyr Thr Ala Asp Phe Pro Ala Ser
                            420                 425                 430

Pro Leu Glu Pro Phe Asn Tyr Thr Gly Thr Pro Asn Asn Thr Asn
                                435                 440                 445

Val Ser Asn Gly Thr Arg Val Val Leu Pro Tyr Asn Ala Ser Val
        450                 455                 460

Glu Val Val Leu Gln Asp Thr Ser Ile Leu Gly Ala Glu Ser His Pro
        465                 470                 475                 480

Leu His Leu His Gly Phe Asp Phe Phe Val Val Gly Gln Gly Thr Gly
                            485                 490                 495

Asn Tyr Asp Pro Ser Lys His Pro Ala Glu Phe Asn Leu Val Asp Pro
                        500                 505                 510

Val Gln Arg Asn Thr Val Gly Val Pro Ala Gly Gly Trp Val Ala Ile
                    515                 520                 525

Arg Phe Phe Ala Asp Asn Pro Gly Val Trp Phe Met His Cys His Leu
                530                 535                 540

Glu Val His Thr Thr Trp Gly Leu Lys Met Ala Trp Val Val Asn Asp
        545                 550                 555                 560

Gly Pro Leu Pro Glu Gln Lys Leu Met Pro Pro Ser Asp Leu Pro
                        565                 570                 575

Met Cys

<210> SEQ ID NO 46
<211> LENGTH: 22
<212> TYPE: DNA
<213> ORGANISM: artificial
<220> FEATURE:
<223> OTHER INFORMATION: SCW_04_5b reverse primer

<400> SEQUENCE: 46
tccatgcatg ctgtgtgttc tt                                              22

<210> SEQ ID NO 47
<211> LENGTH: 22
<212> TYPE: DNA
<213> ORGANISM: artificial
<220> FEATURE:
<223> OTHER INFORMATION: SCW_05_5b forward primer

<400> SEQUENCE: 47
```

| | |
|---|---|
| gcaggatcga gacagaggta cg | 22 |

<210> SEQ ID NO 48
<211> LENGTH: 668
<212> TYPE: DNA
<213> ORGANISM: artificial
<220> FEATURE:
<223> OTHER INFORMATION: SCW_04_5b reference sequence

<400> SEQUENCE: 48

| | |
|---|---|
| acagctatga ccatgtccat gcatgctgtg tgttcttatg tacgtatact tgctggctag | 60 |
| gactaggagt acccacatgc atgcatgcat gcatgcatgc atgcacgcac gcacgcagtg | 120 |
| atttagctat agctgctacc tgctagtagc tcttgctgtt gatgcatggt cgtctgttct | 180 |
| tccatcgtct atatatgaag gaagttttgg accacgacgg acgtgacaga cagggtctat | 240 |
| atatcatctg ccgtttcgaa tcatgtcatg tcatgtgtgg tgtgggcttg tgtgtggcat | 300 |
| atatggcagg tgacgatgaa gaaggtgacg cggctgtgca ccacccgcgc catcccgacg | 360 |
| gtgaacggcc agttccccgg ccccaagata gtcaccaggg agggcgaccg cgtcgtcgtc | 420 |
| aaggtgctga acaatgtcaa ggacaacgtt accatccact ggtaaacttt ctcttcatgt | 480 |
| atatagtaat tagtatacat atatatatag cgatctgccc tgcagcaacg acgacgaact | 540 |
| gccatgtttc tttgcaccaa cgacgcgacg aactgcagca gtaacctaga tcatcattcg | 600 |
| caaagctgcc atgtttcaac ggagaaatca tcgtttcgta cctctgtctc gatcctgcac | 660 |
| tggccgtc | 668 |

<210> SEQ ID NO 49
<211> LENGTH: 5382
<212> TYPE: DNA
<213> ORGANISM: Zea mays

<400> SEQUENCE: 49

| | |
|---|---|
| tagacatcgc cgaaaaggtg gagttgacaa gcgtgagttt cccaaccata gacagccaag | 60 |
| tattggtggc attcaacctt ctatcaattt tagaaatgaa aggaagataa tctttaattt | 120 |
| tcgactttgt gtgatccata ggcaaaccca gtaggtgaa agaggaagca ccaacttggc | 180 |
| aaccaaacat tgcagccaac tgaccgtttt tgacggtgtc gaggttgatc ggcagaagac | 240 |
| aagacttgtg gaarttgatt ctgaacccag ttgcaagcaa gaaagggtgg aaaattcctt | 300 |
| tcagacagaa caaatctctt tggtacgcct tcatgatgat aagagtgtca ttagcgtatt | 360 |
| ggataatcgg gaagtcggac atgttgtccc tctcaagggg acaacgaaaa cacccatatt | 420 |
| ggrtaccta ttaatgatgc actaaagaag atcaacaacg attaagaaaa ggagaggaaa | 480 |
| caagggtcc cctaagaaaa ggagaggaaa caagggtcc cctatcggac acctcttttg | 540 |
| cacaataaac ttttacctaa cacctcattc agcaacacag ccgaggcact agactgaagg | 600 |
| atggcttgaa tccaggaaat ccattctctcc gggaagccga gatgcttata catttccaga | 660 |
| ctagcactgt gccccccctt agaggagaat ttcccctggc aatgttaaat agagatgcat | 720 |
| attgtctttt gaggrtcagg ttttcaaatc acttgtccac atagaatcta acccaagccc | 780 |
| cattatgaag attgaaaatg gataaatcca aaaaatgaca tttatccttt ataaggcttg | 840 |
| gcctcaatag agtgagcctc ctagtttcca atgtgttttct cctataattt tatctttcaa | 900 |
| cgcaagtaca tcttcctaag aagttttgtc actacacatc caaaccacat caacattgat | 960 |
| aagtttgaat taccatttat tttgcgaaca atgattttg aatttcaaga tgaacaatta | 1020 |
| ctaagccatc ttactccttt gtaaacatag aatatctcac ttggtcaact tgttttttt | 1080 |

```
tgaaaccata tttattgagt tcgaattgca acaaaggatt tcaaactact ccagatgaaa    1140
aaaaatctat gtgaaagtaa acaatgatt tcctatcaca aaacacaact tttaaaacct     1200
ttagaagaat gaagaagaaa caatgcatag agaaaccaca aagcctcttt aaacgctgtg    1260
tacgacgcta tatgtacgac gacaatgtgt atctccattg atatgtttat gcagtagaaa    1320
cgaatcataa tgttggacaa tgtcaacgcg cggtggatct tcagcacttg gaagatcgg     1380 ccggcggcgg catcagcttc tgctcaggca acgggccatc gttgaccacc catgccatct    1440
tcaaccccca gcttgtgtgc acctccagat ggcaatgcat gaaccaaaca cctgcacaac    1500
aatatatttt ttcccgagaa gcacaaacga attgagtgtc tagccagttg ttgagtggcg    1560
cttgcaatta attggctatt tggacggagg gagtagcaca caatgtaatt ttagggcttg    1620
ttcggttaga gatggattaa tatagattga aggggattaa atctcctctt atacaaattt    1680
ttgttataaa aatttaataa aacctaagat gctttgacta tactggaatg atttgtcatt    1740
tggacggcaa ttttagctag ctggctgttc acgcaccggg attatccgcg aagaacctga    1800
tggcgaccca gcccctgcc ggcacgccga cggtgttcct ttgcaccggg tcgactaggt     1860
tgaacttggg tgggtccttg gacgagtcgt agttgccgaa gccttggccg acgacgaaga    1920
aatcgaatcc gtggaggtgc agcgggtggc tctcggcgcc gaggatgctg gtggcctgca    1980
gcacgacctc gacgctggta ttgtagtcca gcaccaccac cttggtcccg tgggagacgt    2040
tggtgttgtt cggcggcgtg cccgtgtagt tgaacggctc gagcggcgcg acggggaagt    2100
cgggcgtgta cacgccggcg acgctgccgt agtgcgcctg caggagcgcg gtggtgggca    2160
tgttgaagga cacgttgttc atggacgccg tgaacatggt cccgttgggc ccctggcacg    2220
tctggttgac ggggcagggg ttggtgccga gcccgacggc gaagaagaag gagcggtcca    2280
cggcgcgggg cacgttggcc gggtagtccg gggttgccag gctccggagc ctggcgctgt    2340
agttcgcggc gaaggccgtg tcgttgagcg cggggagcga gggccggaag agcgggaggc    2400
tcctgatgtg gcccggcggc gcgtactcga gcacggccgc gacggtggtg ttgtcgaagg    2460
tgcccggctg gcccgtgccg taggggcgcg ccagcatgag gtgcgtggcc gcggggcacc    2520
ccgcgtcggg ctcggcgcgc aggagcacgt tggtggtctg gcccggcgtg atgagcacga    2580
tgtccgtgcg gaacggcttg acgtaggcgg cgtcgacgtc gacgacggtg agcgtgtggt    2640
tggcgatgga gaagaagagc tcgtcgttga gcgcggcgtt gatgagacgg agcaggtacc    2700
atttgccggg cagcaccttc agcttgaacg tgtctatgga agcagcacac atgtgacaca    2760
tgacggtgag cttgaacttt tcaatgggcc ctggctgaac gggccgagtc ttacctttgc    2820
tggagcagtt gtacaaaggg cccgggagcc cgttgatggt gaaggcgtcc gacacgtttg    2880
ggcctgctcc agtctgaagc gcctgggcga caattgtctc tggatccgcg ttgaaccact    2940
ctcctgcggc cacatcgcac gttaattatc ctagtagtac agggcaggct acaagcagag    3000
cagagcagca gcagcagcag caccgaagat gactgggacg tccttgtagg gtttaaccgg    3060
gagcgggtat ggcacgccgc gcttggggag gatgacgatg gccccgtaga gcgtggcgcg    3120
catccaggag acgtgcgcgt gccagaacag ggtgccccgc tgcccgtga tggtgaagtt     3180 gtacacgaag ctctgccccg tctggatggg gcactgcgtc acgtacgccg gcccgtccga    3240
ccaccccgtg cgcagctgcc gaacgccgtg cctgttgttc aattcgttcg cgtgtacgta    3300
tatgcagttt gcatcgcacg cacccagagg gaaggcacac aaaagcatca gtacgggcat    3360
gcaaatatat atcagctgca ttatattgca ttggcacgtc ctgaaagacc tgaaactagg    3420
ctgctgccca cttggtcctt tgctaactga aaggatggcg agctagctgc tgatcgcatc    3480
```

```
caggaaacaa ataaaaaggt ggtagacgct gcttgttatt aattagttgc tgacaccaac   3540
cagcaggatc gagacagagg tacgaaacga tgatttctcc gttgaaacat ggcagctttg   3600
cgaatgatga tctaggttac tgctgcagtt cgtcgcgtcg ttggtgcaaa gaaacatggc   3660
agttcgtcgt cgttgctgca gggcagatcg ctatatatat atgtatacta attactatat   3720
acatgaagag aaagtttacc agtggatggt aacgttgtcc ttgacattgt tcagcacctt   3780
gacgacgacg cggtcgccct ccctggtgac tatcttgggg ccggggaact ggccgttcac   3840
cgtcgggatg gcgcgggtgg tgcacagccg cgtcaccttc ttcatcgtca cctgccatat   3900
atgccacaca caagcccaca ccacacatga catgattcga aacggcagat gatatataga   3960
ccctgtcacg tccgtcgtcc caaacttcct tcatatatag acgatggaag aacagacgac   4020
catgcatcaa caacaagaac tactagcagc tatagctaaa tcactgcgtg cgtgcgtgca   4080
tgcatgcatg catgtgggta ctcctagtcc tagccagcaa gtatacgtac ataagaacac   4140
acagcatgca tggacgaacg gcggctgctt aattggttga tgagtgaaat gcacttacgt   4200
tgaaggtgta gtgtctggtt gtgccgccgc cgtgtgacga ctgcggcaac gctaccaacg   4260
tgccgaagaa caggatgaac gcaagccacg acgatggcgg cgccgccccc atctcccttc   4320
ccttggcacg cagatcgatc tcggacgaga gatcgaggac gtacggttgt tatatatggc   4380
cggccgcagc aagatagcta gctagagcta tagctacaac acgcggcagg aatgaagggt   4440
tatatagcga ggaggaggag gacagtacag tactgacgac ggtggttgca ttccttcctt   4500
ccttccttgc aatttattag gtggcgacat gatattttcc cttttttttcc cagtgacaag   4560 aaaaaaccgg ggcggagcga gaattaggtg acgatgatga tcgaaagggt gttgacagga   4620
gacggagaaa aaggcgggc ttattagcgc cagccagcgg ccgcttttgc ctggtcatgt   4680
acaaagagtt gggtccgcct ggattttaga gtgcaggcaa aggaatcgcc ctttttgacg   4740
tatggccccg ctagctgctt gctctcgctc tggacggacg tacatgtatt ttctccggcg   4800
tccagcgcgc tcattttttt tttgaaccgt tcgatctgag tgcaccctcg tcaggattca   4860
ggaatcatga ctcatgactg agactactga gatgatgcag ccagccaatt atctccaacg   4920
tacgtattac agactgaagc ccgcgcccgc ccccctgca gtgttgtgat atgatcttgt   4980
gtgttcttct caaggaacga ccgcaaatta accgtcgcgt cgtctgttga gatttccttg   5040
tcgcgtcaga tcgaacgcta ccttattaac acttggctag gattggagtg ctcagcggtt   5100
aatttcaaca gttttctcc tgtaaactga tagacggacg aactagagat cagagtttag   5160
aacactgcag ctcacaggtc caggccacct ctctgttgga ttgatcttat gtgaatccgg   5220
tcaaagaggg gacttcttgt attatgattg catgcataac aatacattgg attattggtt   5280
aacattcctc gccccataaa cctagggacc tgatctactc taatacggct agcgatggaa   5340
agaccataac ctagctaatg cactctcggt gtcgtcgtcg ct                      5382
```

<210> SEQ ID NO 50
<211> LENGTH: 21
<212> TYPE: DNA
<213> ORGANISM: artificial
<220> FEATURE:
<223> OTHER INFORMATION: PHM13936 forward external primer

<400> SEQUENCE: 50
aaggaacgga tattacaagc g                                              21

<210> SEQ ID NO 51
<211> LENGTH: 22

```
<212> TYPE: DNA
<213> ORGANISM: artificial
<220> FEATURE:
<223> OTHER INFORMATION: PHM13936 forward internal primer

<400> SEQUENCE: 51
gagagcttgt tatatcttct ac                                               22

<210> SEQ ID NO 52
<211> LENGTH: 20
<212> TYPE: DNA
<213> ORGANISM: artificial
<220> FEATURE:
<223> OTHER INFORMATION: PHM13936 reverse internal primer

<400> SEQUENCE: 52
cagcaagtct gacccttgtt                                                  20

<210> SEQ ID NO 53
<211> LENGTH: 22
<212> TYPE: DNA
<213> ORGANISM: artificial
<220> FEATURE:
<223> OTHER INFORMATION: PHM13936 reverse external primer

<400> SEQUENCE: 53
acttagctat atcttcttca cc                                               22

<210> SEQ ID NO 54
<211> LENGTH: 21
<212> TYPE: DNA
<213> ORGANISM: artificial
<220> FEATURE:
<223> OTHER INFORMATION: PHM15671 forward external primer

<400> SEQUENCE: 54
gccaattacc gtctatgaga g                                                21

<210> SEQ ID NO 55
<211> LENGTH: 20
<212> TYPE: DNA
<213> ORGANISM: artificial
<220> FEATURE:
<223> OTHER INFORMATION: PHM15671 forward internal primer

<400> SEQUENCE: 55
tggaggttca caccagacta                                                  20

<210> SEQ ID NO 56
<211> LENGTH: 21
<212> TYPE: DNA
<213> ORGANISM: artificial
<220> FEATURE:
<223> OTHER INFORMATION: PHM15671 reverse internal primer

<400> SEQUENCE: 56
gaggccataa aggcactaaa t                                                21

<210> SEQ ID NO 57
<211> LENGTH: 22
<212> TYPE: DNA
<213> ORGANISM: artificial
<220> FEATURE:
<223> OTHER INFORMATION: PHM15671 reverse external primer

<400> SEQUENCE: 57
aaatgagcct ctcaatatga tg                                               22
```

```
<210> SEQ ID NO 58
<211> LENGTH: 22
<212> TYPE: DNA
<213> ORGANISM: artificial
<220> FEATURE:
<223> OTHER INFORMATION: PHM14875 forward external primer

<400> SEQUENCE: 58
gatataatta ctgctggaat gg                                              22

<210> SEQ ID NO 59
<211> LENGTH: 21
<212> TYPE: DNA
<213> ORGANISM: artificial
<220> FEATURE:
<223> OTHER INFORMATION: PHM14875 forward internal primer

<400> SEQUENCE: 59
gtcagagttg ttgatcatca g                                               21

<210> SEQ ID NO 60
<211> LENGTH: 20
<212> TYPE: DNA
<213> ORGANISM: artificial
<220> FEATURE:
<223> OTHER INFORMATION: PHM14875 reverse internal primer

<400> SEQUENCE: 60
tcggattcag tatgtccagc                                                 20

<210> SEQ ID NO 61
<211> LENGTH: 21
<212> TYPE: DNA
<213> ORGANISM: artificial
<220> FEATURE:
<223> OTHER INFORMATION: PHM14875 reverse external primer

<400> SEQUENCE: 61
aactcgcttc aaggatgagg a                                               21

<210> SEQ ID NO 62
<211> LENGTH: 20
<212> TYPE: DNA
<213> ORGANISM: artificial
<220> FEATURE:
<223> OTHER INFORMATION: PHM11079 forward external primer

<400> SEQUENCE: 62
gcgttgacga ttttcagatt                                                 20

<210> SEQ ID NO 63
<211> LENGTH: 21
<212> TYPE: DNA
<213> ORGANISM: artificial
<220> FEATURE:
<223> OTHER INFORMATION: PHM11079 forward internal primer

<400> SEQUENCE: 63
gagaagaagc taaccatcga t                                               21

<210> SEQ ID NO 64
<211> LENGTH: 22
<212> TYPE: DNA
<213> ORGANISM: artificial
<220> FEATURE:
<223> OTHER INFORMATION: PHM11079 reverse internal primer
```

```
<400> SEQUENCE: 64
atctgcacac gttaacatac at                                              22

<210> SEQ ID NO 65
<211> LENGTH: 22
<212> TYPE: DNA
<213> ORGANISM: artificial
<220> FEATURE:
<223> OTHER INFORMATION: PHM11079 reverse external primer

<400> SEQUENCE: 65
gcactattac tatattgcat ag                                              22

<210> SEQ ID NO 66
<211> LENGTH: 21
<212> TYPE: DNA
<213> ORGANISM: artificial
<220> FEATURE:
<223> OTHER INFORMATION: PHM15150 forward external primer

<400> SEQUENCE: 66
tattccattg atggtagcag c                                               21

<210> SEQ ID NO 67
<211> LENGTH: 21
<212> TYPE: DNA
<213> ORGANISM: artificial
<220> FEATURE:
<223> OTHER INFORMATION: PHM15150 forward internal primer

<400> SEQUENCE: 67
agcagctaat taaccagtcc t                                               21

<210> SEQ ID NO 68
<211> LENGTH: 22
<212> TYPE: DNA
<213> ORGANISM: artificial
<220> FEATURE:
<223> OTHER INFORMATION: PHM15150 reverse internal primer

<400> SEQUENCE: 68
atactaagct caagatagta gg                                              22

<210> SEQ ID NO 69
<211> LENGTH: 22
<212> TYPE: DNA
<213> ORGANISM: artificial
<220> FEATURE:
<223> OTHER INFORMATION: PHM15150 reverse external primer

<400> SEQUENCE: 69
ggtgctgaaa accaaataat gt                                              22

<210> SEQ ID NO 70
<211> LENGTH: 22
<212> TYPE: DNA
<213> ORGANISM: artificial
<220> FEATURE:
<223> OTHER INFORMATION: PHM1239 forward external primer

<400> SEQUENCE: 70
ttgaggctac atatctggta ga                                              22

<210> SEQ ID NO 71
<211> LENGTH: 21
```

```
<212> TYPE: DNA
<213> ORGANISM: artificial
<220> FEATURE:
<223> OTHER INFORMATION: PHM1239 forward internal primer

<400> SEQUENCE: 71
ttgttgtgtc tggaagcaga t                                          21

<210> SEQ ID NO 72
<211> LENGTH: 20
<212> TYPE: DNA
<213> ORGANISM: artificial
<220> FEATURE:
<223> OTHER INFORMATION: PHM1239 reverse internal primer

<400> SEQUENCE: 72
aagaggaacc cacagatgct                                            20

<210> SEQ ID NO 73
<211> LENGTH: 21
<212> TYPE: DNA
<213> ORGANISM: artificial
<220> FEATURE:
<223> OTHER INFORMATION: PHM1239 reverse external primer

<400> SEQUENCE: 73
ctgcagcata cctgtataac c                                          21

<210> SEQ ID NO 74
<211> LENGTH: 20
<212> TYPE: DNA
<213> ORGANISM: artificial
<220> FEATURE:
<223> OTHER INFORMATION: PHM9528 forward external primer

<400> SEQUENCE: 74
ccagacatgg aggacattgt                                            20

<210> SEQ ID NO 75
<211> LENGTH: 20
<212> TYPE: DNA
<213> ORGANISM: artificial
<220> FEATURE:
<223> OTHER INFORMATION: PHM9528 forward internal primer

<400> SEQUENCE: 75
caagtacggc atggtgttgt                                            20

<210> SEQ ID NO 76
<211> LENGTH: 22
<212> TYPE: DNA
<213> ORGANISM: artificial
<220> FEATURE:
<223> OTHER INFORMATION: PHM9528 reverse internal primer

<400> SEQUENCE: 76
tccctatatg caattctgca ca                                         22

<210> SEQ ID NO 77
<211> LENGTH: 22
<212> TYPE: DNA
<213> ORGANISM: artificial
<220> FEATURE:
<223> OTHER INFORMATION: PHM9528 reverse external primer

<400> SEQUENCE: 77
cttgacatgt acaagtacaa ta                                         22
```

```
<210> SEQ ID NO 78
<211> LENGTH: 19
<212> TYPE: DNA
<213> ORGANISM: artificial
<220> FEATURE:
<223> OTHER INFORMATION: PHM14541 forward external primer

<400> SEQUENCE: 78
agttcgagcc ggaggtgaa                                            19

<210> SEQ ID NO 79
<211> LENGTH: 20
<212> TYPE: DNA
<213> ORGANISM: artificial
<220> FEATURE:
<223> OTHER INFORMATION: PHM14541 forward internal primer

<400> SEQUENCE: 79
tcagggccta ttacttggga                                           20

<210> SEQ ID NO 80
<211> LENGTH: 19
<212> TYPE: DNA
<213> ORGANISM: artificial
<220> FEATURE:
<223> OTHER INFORMATION: PHM14541 reverse internal primer

<400> SEQUENCE: 80
tcgaggccgt tggtcgtgt                                            19

<210> SEQ ID NO 81
<211> LENGTH: 20
<212> TYPE: DNA
<213> ORGANISM: artificial
<220> FEATURE:
<223> OTHER INFORMATION: PHM14541 reverse external primer

<400> SEQUENCE: 81
ttcatgagct ccaggtcgaa                                           20

<210> SEQ ID NO 82
<211> LENGTH: 20
<212> TYPE: DNA
<213> ORGANISM: artificial
<220> FEATURE:
<223> OTHER INFORMATION: PHM2690 forward external primer

<400> SEQUENCE: 82
atccatgacg ggccatacaa                                           20

<210> SEQ ID NO 83
<211> LENGTH: 20
<212> TYPE: DNA
<213> ORGANISM: artificial
<220> FEATURE:
<223> OTHER INFORMATION: PHM2690 forward internal primer

<400> SEQUENCE: 83
aaggtgaaga gcgaggagga                                           20

<210> SEQ ID NO 84
<211> LENGTH: 20
<212> TYPE: DNA
<213> ORGANISM: artificial
<220> FEATURE:
<223> OTHER INFORMATION: PHM2690 reverse internal primer
```

-continued

```
<400> SEQUENCE: 84
agtacatgct ccatctcctg                                              20

<210> SEQ ID NO 85
<211> LENGTH: 20
<212> TYPE: DNA
<213> ORGANISM: artificial
<220> FEATURE:
<223> OTHER INFORMATION: PHM2690 reverse external primer

<400> SEQUENCE: 85
cccgcagtgt gcacaatcaa                                              20

<210> SEQ ID NO 86
<211> LENGTH: 22
<212> TYPE: DNA
<213> ORGANISM: artificial
<220> FEATURE:
<223> OTHER INFORMATION: PHM1241 forward external primer

<400> SEQUENCE: 86
gttcttcaaa ttcatcagaa gg                                           22

<210> SEQ ID NO 87
<211> LENGTH: 21
<212> TYPE: DNA
<213> ORGANISM: artificial
<220> FEATURE:
<223> OTHER INFORMATION: PHM1241 forward internal primer

<400> SEQUENCE: 87
tctagtgtga agcgtagtag c                                            21

<210> SEQ ID NO 88
<211> LENGTH: 22
<212> TYPE: DNA
<213> ORGANISM: artificial
<220> FEATURE:
<223> OTHER INFORMATION: PHM1241 reverse internal primer

<400> SEQUENCE: 88
tttctagacc acttctcctt ag                                           22

<210> SEQ ID NO 89
<211> LENGTH: 22
<212> TYPE: DNA
<213> ORGANISM: artificial
<220> FEATURE:
<223> OTHER INFORMATION: PHM1241 reverse external primer

<400> SEQUENCE: 89
gctaaatgat ggaatattag cc                                           22

<210> SEQ ID NO 90
<211> LENGTH: 22
<212> TYPE: DNA
<213> ORGANISM: artificial
<220> FEATURE:
<223> OTHER INFORMATION: PHM11733 forward external primer

<400> SEQUENCE: 90
atgctgtagc tattgacctt ga                                           22

<210> SEQ ID NO 91
<211> LENGTH: 20
```

```
<212> TYPE: DNA
<213> ORGANISM: artificial
<220> FEATURE:
<223> OTHER INFORMATION: PHM11733 forward internal primer

<400> SEQUENCE: 91
gtgatgaagt caaccagcgt                                                    20

<210> SEQ ID NO 92
<211> LENGTH: 21
<212> TYPE: DNA
<213> ORGANISM: artificial
<220> FEATURE:
<223> OTHER INFORMATION: PHM11733 reverse internal primer

<400> SEQUENCE: 92
ctgataataa ataaggatgc c                                                  21

<210> SEQ ID NO 93
<211> LENGTH: 21
<212> TYPE: DNA
<213> ORGANISM: artificial
<220> FEATURE:
<223> OTHER INFORMATION: PHM11733 reverse external primer

<400> SEQUENCE: 93
ctgatatccg agacatctca g                                                  21

<210> SEQ ID NO 94
<211> LENGTH: 738
<212> TYPE: DNA
<213> ORGANISM: artificial
<220> FEATURE:
<223> OTHER INFORMATION: PHM13936 reference sequence

<400> SEQUENCE: 94
tcatgacacc cttttaccct gttatatctt ccctgtatac ttctacaaaa actagaacac         60
agaagtaatt attgttctat tatccttcta gtctttttt attgcaactg atttgattta        120
ccatcttagg ggcaatattg aagatgcatt gcagaaaata caggtatgct tcttcaattc       180
aatttcattt tctagggcta gaccacttac attactccac aatttgtcct gaacaggcaa       240
tcattgatgc tgcatcatat gttcctccac ccccaacaga agaccaaaag aaaaagattg       300
aaaaaatgta agctgtttat ttcactagtt gttttccttct aattcatgtt tcaattagta      360
attatatggc ataaactgca ccaaagtgct caataatatc taatcctgaa gtgaattcaa       420
gtgacacaga cacacagtat atgattttct tcaacttctg atgctctaaa gttcctgtac       480
ttctgcattg ccacaactta tgaggagac gatcatatct ttcatatatt tcatggattt       540
actttgaagt gcttcagtat tgcattttcc aaggttaaat gcacaaaatg tgtagaaaag       600
ctgtactgta ttactgttag ttgcagttaa gaatggcatt gcaattgcca gtaatttatt       660
gcccaaaacg tttggggttg tttcttcagg agatctttaa atcctccggg gttgtaaggg       720
ccaaatcttt actgtccc                                                    738

<210> SEQ ID NO 95
<211> LENGTH: 531
<212> TYPE: DNA
<213> ORGANISM: artificial
<220> FEATURE:
<223> OTHER INFORMATION: PHM15671 reference sequence

<400> SEQUENCE: 95
aaaggggaaa attcccagtc acgacgtgga ggttcacacc agactaccat ttcccgggat        60
```

```
ttcacctaca ttgatgacat tgtgaagggg tgcgtagcgg ccttggatac agctggtcgg      120
agcacaggca gtggaggcaa gaagcgaggt acggcaccgt tcaggactta caatttgggc      180
aacacttcac ctgtgcctgt tacacagcta gtggatttgc tggagaaact gctcaaagtg      240
aaggctgtga ggaaagttgt taagatgcca aggaatggag atgtgccata cacgcatgct      300
aatgtaagcc ttgcacaacg ggagctcggt taccatccat ccacagatct gcaaacaggc      360
ctcaagaagt ttgtgcggtg gtaccttgag tactaccatc ctgagctggc tgagaagcag      420
aagctgcgta ccagtagcaa tggcaagggt tcacgtggtc gcaatggcag ctcaattagc      480
gcaagatgac tgtgtatttta ggccttagcc taatttaaat aaaaaaaaaa a              531

<210> SEQ ID NO 96
<211> LENGTH: 676
<212> TYPE: DNA
<213> ORGANISM: artificial
<220> FEATURE:
<223> OTHER INFORMATION: PHM14875 reference sequence

<400> SEQUENCE: 96 cgaccccccat cgttaagttg ttgatatcag gtagatgcaa tacacattga tggaacgttg       60 cttttctgatg tagaaactct tgcagtttag tgttttatta tctgaccaag gagatataat      120
tttgcagcgt ctaagcagct ctggatatgt tttctctgca tctctgccac cttatcttgc      180
cactgctgct gtttctgctg tcaactacct ggagcagaat cccgcagttc ttgcaaatct      240
aaggagcaat attgctcttt tgcataaagg taagctgatt ctattgttaa ttaattattt      300
ctttgaccag gttgtacttc tcatttttct gggttaatgt ggaaaatatg gcataacac       360 cgaggcaact acctaacagt aaatctttaa agtatacaga agccacagtg aattacaatg      420
taacttcttt tctctctgag ctctaggttc ctataccagg gaaaatatga ttaagttgtg      480
aaactaatat aagccataac tagtgtgttc atgcacaata cgatttccaa ctactatgta      540
accaactggt ggccaccatc tcaacactct ttgtattcac tctgcagaat tatcagatac      600
tccagggcta aaaattttca gccatgttct gtcacctatt gtcttcctta agctgaaaaa      660
atcgacaggt tcccct                                                      676

<210> SEQ ID NO 97
<211> LENGTH: 503
<212> TYPE: DNA
<213> ORGANISM: artificial
<220> FEATURE:
<223> OTHER INFORMATION: PHM11079 reference sequence

<400> SEQUENCE: 97
gggaaggtcc cagtcacaac ggagaagaag ctaaccatcg atcaagaatt tgagcagtat       60
tttgcgaacc tcatgctgta ggatcgagtg gataattttg tgacagaaat ggcgttgcga      120
catccaaaca tggtttgctt gctgagcaaa gtggcgaacc ttggctacca ttggagctat      180
cgttctatgg tgctgtttgg taacataaat ggtaatgata taattcaca cctgagtacc       240 aacgacccga gtaccaacgg taacaagttt aaataggtcg atattagttc ttagtgtggt      300
atctgattac gattggattt aaacaaacat aatttaatgt ttatcggtta cttattacat      360
tacaaatatg tgaaccaaac ggcacatatt tgtacaccga gtcctatcac ttaatgtata      420
tacgtgtgaa atgtgtatct tttccagctt gtccatcaaa tgttgcatca tgatgtatgt      480
aacgttgcaa actttgctaa taa                                              503
```

```
<210> SEQ ID NO 98
<211> LENGTH: 546
<212> TYPE: DNA
<213> ORGANISM: artificial
<220> FEATURE:
<223> OTHER INFORMATION: PHM15150 reference sequence

<400> SEQUENCE: 98
ggggaaggtc ccagtccaac aagcagctaa ttaaccagtc ctgctatgtt atagcatgtg      60
gaccttgacc tgtgaacctg tctgatcaag gtaaacacta acccaagttt ggtgcaatgt     120
taaacaaatc aagggtgtag ttgtaccgta tagcatttat aaataatgtg ggcctaatag     180
tcctgttctc aggacagaat ttttgacaat gacataaaaa tgttttaatc tgcaggaaat     240
ggcttgaaga cggataatga tcaacatgga gctttgctag cttcacatct gtccagccag     300
tactctgata gactgggtgt agacctctct accttggtgt tggtaccatt acttctatta     360
aatttcgtag ttttcttctt tccatttact tctatgatcg gcctggcgtc ctattagcaa     420
taaccagatc actgcttcta gttaattgtt agccaaacta cctactatct gagcttataa     480
ttagcaataa ccagatcact gcttctagtt aattgttagc caaactacct actatctgag     540
ctataa                                                                546

<210> SEQ ID NO 99
<211> LENGTH: 554
<212> TYPE: DNA
<213> ORGANISM: artificial
<220> FEATURE:
<223> OTHER INFORMATION: PHM1239 reference sequence

<400> SEQUENCE: 99
cccatcagaa ccttgttgtg tctggaagca gatttgaact ggcatggatg tagaccgtta      60
agggtggtac caagcaaaat ggacttatta atacattctt gtgtgcataa acttaccatt     120
tcttactaga aggaatagtc aaattatctc caattaaacc taattcaaaa cagttcaatg     180
taatggagcc aacttgttga ttattaagtc accaaattat ataggtggag ataaactttg     240
gggagtttta actgatggcc tgtttggtac atgccaatgc tctgtatatg gtaacacacc     300
aagcatttgc tagttgctac taggattagc caaatcatta tcatattgct tgggatctgt     360
gaattggtta cttaacactg aactgcatgc tcgagtgtca tttagtgctc tttgctctta     420
tgttgtacct tttcttgcag gctatccatg atttttgcct acaaaggtg attgaaaagg      480 ggggaggatg aaggggagg acaccacgga gttgttttgg catgcagcat ctgtgtcctt     540
acttttcgtt ataa                                                       554

<210> SEQ ID NO 100
<211> LENGTH: 508
<212> TYPE: DNA
<213> ORGANISM: artificial
<220> FEATURE:
<223> OTHER INFORMATION: PHM9528 reference sequence

<400> SEQUENCE: 100
aaggaaaatc ccagtcaaaa cgcaagtacg gcatggtgtt gttggagata ttgaccggaa      60
gagttccttc ctccgaggat gacggaccac tggaaaattg ggtgtctcgc tattttgaag     120
gcgggatgcg tcttgaggag ctgattgacc ctagcatcgg cttcttcccc gaggacactg     180
cacgagccct ttgtgaggtt gtgaggtcct gcattgatcg ggatccaaag aagagaccgc     240
agatgaaaga ggtcgcagct cggatgagag agatcaccgc gctggggcct gatgggcaa      300 ctccgaaggt gtcaccgctc tggtgggctg agcttgagat tatgacttct gagagctgag     360
```

```
ttcgacgcat gccagatgat attgtttctc ctagtgtgac tgagaattct ttgagctact    420
actggctgct gctaatcttg tttgtggaag tggtgattag gtagaatttg ttatgtgtgc    480
agaattgctt ttggactttc ttaatacc                                      508
```

<210> SEQ ID NO 101
<211> LENGTH: 576
<212> TYPE: DNA
<213> ORGANISM: artificial
<220> FEATURE:
<223> OTHER INFORMATION: PHM14541 reference sequence

<400> SEQUENCE: 101

```
ccgtgtgaaa accagggcct attacttggg acccaaaggc gagaagcttc tggtgttcga     60
ctacatgccc aaaggcaacc ttgcttcttt cctccatggt aagctcactt gcacagttct    120
ctttagactt tagctatctg ttagcttctt tttttctgct taacgaaact tcgccttttg    180
tattatcgca gctcgtgcac cggacagcag cccggtggac tggccgacga ggatgaacat    240
cgcgatgggc cttgcgcggg gattgcacca cctacacacc gacgccaaca tggtgcacgg    300
caacatcacc agcaacaaca tcctcctgga cgaggggaac gacgccaaga tcgccgactg    360
cggcctgtcg cgcctcatga gcgcggcagc caactccagc gtgatcgccg ccgcgggcgc    420
gctcggctac cgcgcgcccg agctctccaa gctgaagaag gccaacacca aaaccgacat    480
ctacagcctc ggggtggtca tgctcgagct cctgaccggc aagtcgcccg acacaccaa     540 cgcctaaatg gggaaaaaag ggaaaggggg gsgaaa                             576
```

<210> SEQ ID NO 102
<211> LENGTH: 623
<212> TYPE: DNA
<213> ORGANISM: artificial
<220> FEATURE:
<223> OTHER INFORMATION: PHM2690 reference sequence

<400> SEQUENCE: 102

```
ccccacagag taaatcagga ggagctgacg gctgctattg agacagcgct aggggagaag     60
aaggactgcc tgtgcttcat cgaggtgatc gcgcacaagg acgacaccag caaagagctg    120
ctggaatggg gctctagggt ttctgccgcc aactcccggc caccaaatcc tcagtagaag    180
tcccgcaggc tccaagcctc ggagtgccag tagtgatagt aagctgtagc acggtggggg    240
ctcaaccgaa taacgtgaac gcattgcccct ttctgttacg tgttttattt tattgtgttt    300
ctgtggtcgt atatctgttt tgtgacgtgt tcccttgctt ctcccatgtg aattccagaa    360
gaactatgag aaatttcagg ttggtgatca ctcatctgtg ttgtcactat ttgtgctgcg    420
ttaccggtgt gattttactg atccaggtaa acatcgccgg ccagggagtg aatcatctag    480
agattgggca tataagtatt gtagcgataa tctaatctag cggttacgga tgtgattcat    540
tctaattggt ggctttaatc catatcgact tctactactt ctagtgttta tgtttacaat    600
tcactttcat tctaattaat ggt                                            623
```

<210> SEQ ID NO 103
<211> LENGTH: 677
<212> TYPE: DNA
<213> ORGANISM: artificial
<220> FEATURE:
<223> OTHER INFORMATION: PHM1241 reference sequence

<400> SEQUENCE: 103

```
gcggcgcgcc ccggtttgtt taagcgtagt agcggtagtg ttgaagctgg tcaaaatggt     60
```

```
aatgcaacgg attctatgta cagaagcaac tcacaaagcg atggtgtcaa ttggagcagt      120
attccttttg atcgatcaaa cagttgtcaa gaaggccgga gctccgacaa gaacatagat      180
agtgcacgtg caagcttagc tcatcggagt aattcatgct tatctgctgt ccaagactct      240
gaaaccgctg ttgtttcagt agataggcat ggagatccca ttacttcact tgtttgttct      300
agcagtggtt tggaaagtca tggctgtgag cctagtggat cagccaccac ctcaggtaat      360
caacagctat tggatttgaa cctggcagcg atatttcagg acagattaaa tgatccaagg      420
atttcatcta tgctaaaaaa gaacggtgga cttggagatg tagaactggc taatcttctt      480
caggataaag gactagatcc aaattttca tacatgctga aagacaaagt tatggatcca      540
cgtattttag ctttgctaca gaggagcagc ttggatgcag atagagagca tcaagatgac      600
gtaaatttca cagctactgg ttcaggtaga ttgggtaccc ctattgcaaa tcaaatttcc      660
ctgtcaaaaa ctagggg                                                    677

<210> SEQ ID NO 104
<211> LENGTH: 457
<212> TYPE: DNA
<213> ORGANISM: artificial
<220> FEATURE:
<223> OTHER INFORMATION: PHM11733 reference sequence

<400> SEQUENCE: 104
ttaataatcg gggttaggtc ccagtcacaa cagtgatgaa gtcaaccagc gtatgctttc       60
tgttgaaagg gctgtcaggg atgctcttat cgcgaaagga gagagaaact tcactgatca      120
agagttccct ccagaggatc gttctttatt tgtagatccg atgaatccac ctctgaaact      180
gcaggtatca catgcacatc tcttgctctt gtgaaaaata ttggttaagt tcctgacatg      240
ttttaatttg tgagttttag gttgtttctg agtggatgag gccttctgac atagcaaagg      300
agatatctat cagttgtcag ccttgcttgt tttcgggttc tgtgaattcc tcagatgtgt      360
gtcaggtata ttttctgtt ttcttttttt gtgcagccag aattgtggta aaagggaatt      420
taggcatcct attatataac tttgggctaa taaaatt                               457
```

US 8,633,351 B2

GENETIC LOCI ASSOCIATED WITH CELL WALL DIGESTIBILITY IN MAIZE

CROSS REFERENCE TO RELATED APPLICATIONS

This application claims the benefit of U.S. Provisional Application No. 61/112,203, filed Nov. 7, 2008, the entire content of which is herein incorporated by reference.

FIELD OF THE INVENTION

The present disclosure relates to compositions and methods useful in enhancing cell wall digestibility in plants.

BACKGROUND OF THE INVENTION

Stover, which consists of the non-grain aboveground plant parts of corn (maize), sorghum, or soybean, that are left in a field after harvest, offers an abundant and inexpensive source of fermentable sugars that can be used as substrates for ethanol production. In fact, approximately upward of 275 million metric tons of stover are produced just from maize in the United States every year, two-thirds of which could be utilized for the production of ethanol, butanol, and other fuels or bioproducts (Graham, et al., (2007) "Current and potential U.S. corn stover supplies"; *Agronomy Journal* 99:1-11). However, the ability of cellulolytic enzymes to digest plant biomass to fermentable sugars is dependent on the properties of the plant cell wall, a highly heterogeneous and complex structure consisting of cellulose microfibrils embedded in a matrix of hemicellulose, pectin (only trace amounts in grasses), cell wall proteins, and phenolic compounds such as lignin. Lignin, in particular, being hydrophobic, significantly hinders the enzymatic hydrolysis of cellulose by preventing the swelling of cellulose fibers, thereby reducing the surface area the enzyme can access. Furthermore, it can sequester cellulases, thus preventing their action on cellulose molecules.

A similar problem arises when corn stover is used as silage. Silage is forage biomass that is harvested and fermented for use as winter fodder for cattle and sheep. As corn plants grow, the yield of energy per unit of land area increases, but the availability of energy, in the form of cellulose and hemicellulose, decreases due to lignification. This reduces the digestibility of the dry matter components in the rumen. From an economic viewpoint, the crop should be harvested at maturity, at peak dry matter yield; however, the limitation on digestibility forces harvest to take place at a more immature stage.

A promising target for the improvement of digestibility in silage maize and for the enhanced bioprocessing of corn stover for ethanol production is the lignin biosynthetic pathway. Lignin is formed by polymerization of different monolignols that are synthesized in a multistep pathway. For a more detailed review of the lignin biosynthetic pathway, see Whetton R and Sederoff R (1995) *The Plant Cell*, 7:1001-1013, and Whetten R et al. (1998) *Annu. Rev. Plant Physiol. Plant Mol. Biol.* 49:585-609. A number of studies have shown that manipulation of the number of copies of genes encoding certain enzymes in the lignin biosynthetic pathway modifies lignin quantity and quality. However, laccases, enzymes proposed to participate in the last step of lignin biosynthesis, the polymerization of monolignols (Bao et al. (1993) *Science* 260:672-674), have not been targeted. This is because little is known about the role of laccases in the polymerization of lignin, particularly for monocot species such as *Zea mays*.

Seventeen laccase genes have been identified in the *Arabidopsis* genome, five of which are located in the vicinity of QTLs for the digestibility traits, Klason Lignin/Neutral Detergent Fiber (KL/NDF), KL and NDF, and DINAGZ, or the in vitro digestibility of the non starch and non soluble carbohydrates (Argillier et al. (1995) *Euphytica* 82:175-184; Barriere et al. (2000) *Fourrages* 163:221-238; Barriere et al. (2005) *Plant Science* 168:1235-1245). Five laccases have been identified in maize, ZmLac1, ZmLac2, ZmLac3, ZmLac4, and ZmLac5. However, while the expression patterns of at least four of these genes (ZmLac2, ZmLac3, ZmLac4, and ZmLac5) correlate with maize regions undergoing lignification, no direct link between laccases and lignin polymerization has been established (Caparros-Ruiz et al. (2006) *Plant Science* 171:217-225).

Genes that increase cell wall digestibility can be employed in breeding programs by the introgression of the most valuable alleles at these loci. Hence, it is desirable to provide allelic compositions and methods for identifying maize plants that display increased cell wall digestibility. Plants with increased cell wall digestibility will have enhanced biomass conversion efficiency for ethanol production, and will also have improved silage quality.

SUMMARY

Compositions and methods for identifying and selecting maize plants with increased cell wall digestibility are provided.

In a first embodiment, methods for identifying maize plants with increased cell wall digestibility by detecting a marker locus in the genome of the maize plant using the sequence of the marker locus, a portion of the sequence of the marker locus, or a complement of the sequence of the marker locus, or of a portion thereof, as a marker probe are provided. The marker probe hybridizes under stringent conditions to the contiguous DNA between and including SEQ ID NO:1, or a nucleotide sequence that is 95% identical to SEQ ID NO:1 based on the Clustal V method of alignment, and SEQ ID NO:8, or a nucleotide sequence that is 95% identical to SEQ ID NO:8 based on the Clustal V method of alignment, and the marker locus comprises at least one allele that is associated with increased cell wall digestibility. The marker probe hybridizes under stringent conditions to the contiguous DNA between and including SEQ ID NO:94, or a nucleotide sequence that is 95% identical to SEQ ID NO:94 based on the Clustal V method of alignment, and SEQ ID NO:104, or a nucleotide sequence that is 95% identical to SEQ ID NO:104 based on the Clustal V method of alignment, and the marker locus comprises at least one allele that is associated with increased cell wall digestibility. In some embodiments, the marker probe hybridizes under stringent conditions to a nucleotide sequence that is 95% identical to SEQ ID NO:48, based on the Clustal V method of alignment. In other embodiments, the maize plant belongs to the Stiff Stalk heterotic group. Maize plants identified by this method are also of interest.

In a second embodiment, methods for identifying maize plants with increased cell wall digestibility by detecting at least one marker allele associated with increased cell wall digestibility in the germplasm of a maize plant are provided. The marker locus can be selected from any of the following marker loci: PHM8098, PHM14801, PHM4175, PHM1783, PHM3364, PHM1730, PHM4359, SCW_04_5b, and PHM9167, as well as any other marker that is linked to these markers. Furthermore, the marker locus can be selected from any of the following marker loci: PHM13936, PHM15671, PHM14875, PHM11079, PHM15150, PHM1239, PHM9528, PHM14541, PHM2690, PHM1241, and PHM11733, as well as any other marker that is linked to these markers. The marker locus can be found on chromosome 1, within the interval comprising and flanked by PHM8098 and PHM9167, and comprises at least one allele that is associated with increased cell wall digestibility. Furthermore, the marker locus can be found on chromosome 1, within the interval comprising and flanked by PHM13936 and PHM11733, and comprises at least one allele that is associated with increased cell wall digestibility. In some embodiments, the marker locus is SCW_05_5b. In other embodiments, the maize plant belongs to the Stiff Stalk heterotic group. Maize plants identified by this method are also of interest.

In a third embodiment, methods for identifying maize plants with increased cell wall digestibility by detecting a haplotype in the germplasm of the maize plant are provided. The haplotype comprises alleles at one or more marker loci, wherein the one or more marker loci are found on chromosome 1 within the interval comprising and flanked by PHM8098 and PHM9167. The haplotype comprises alleles at one or more marker loci, wherein the one or more marker loci are found on chromosome 1 within the interval comprising and flanked by PHM13936 and PHM11733. The haplotype is associated with increased cell wall digestibility.

In one embodiment, the maize plant belongs to the Stiff Stalk heterotic group.

Maize plants identified by this method are also of interest.

In a fourth embodiment, methods of selecting plants with increased cell wall digestibility are provided. In one aspect, a first maize plant is obtained that has at least one allele of a marker locus wherein the allele is associated with increased cell wall digestibility. The marker locus can be found on chromosome 1, within the interval comprising and flanked by PHM8098 and PHM9167. The marker locus can be found on chromosome 1, within the interval comprising and flanked by PHM13936 and PHM11733. The first maize plant can be crossed to a second maize plant, and the progeny resulting from the cross can be evaluated for the allele of the first maize plant. Progeny plants that possess the allele from the first maize plant can be selected as having increased cell wall digestibility. Maize plants selected by this method are also of interest.

BRIEF DESCRIPTION OF FIGURES AND SEQUENCE LISTINGS

The invention can be more fully understood from the following detailed description and the accompanying drawings and Sequence Listing which form a part of this application. The Sequence Listing contains the one letter code for nucleotide sequence characters and the three letter codes for amino acids as defined in conformity with the IUPAC-IUBMB standards described in Nucleic Acids Research 13:3021-3030 (1985) and in the Biochemical Journal 219 (No. 2): 345-373 (1984), which are herein incorporated by reference in their entirety. The symbols and format used for nucleotide and amino acid sequence data comply with the rules set forth in 37 C.F.R. §1.822.

FIG. 1 shows the physical map arrangement of sequenced BACs (obtained from the Maize Genome Browser, which is publicly available on the internet) that assemble to the region defined by and including PHM13936 (SEQ ID NO:94) and PHM11733 (SEQ ID NO:104). Non-shaded boxes in FIG. 1 represent sequenced BAC clones, for example B1 designates BAC b0224H06. The number in each non-shaded box represents the BAC clone name, and the numbers are described in Table 2B and Table 2A. The positions of the PHM markers described herein are indicated in FIG. 1 by an asterisk (*) in a particular BAC clone at which it is located and further described in Table 2A and Table 2B. The positions of the following known markers: AY110052, csu859, and umc1397 are also noted in Table 2A and in FIG. 1 by a lightly shaded gray box above the BAC at which it is located. The known markers are contained within the BAC but at a different location then the PHM marker. The position of the laccase-like gene, as represented by the gene-specific marker SCW_04_5b, is also noted in FIG. 1. The gaps (represented by dotted lines) are not gaps in the contiguous stretch of DNA per se but are areas where BACs that have not been sequenced assemble to the physical map.

FIG. 2 shows the results from a whole genome scan for marker-trait associations with cell wall digestibility (NDFd), as measured using wet chemistry, in a Stiff Stalk subpopulation. X axis: distance expressed in cM on Chr. 1. Y axis: probability value.

FIG. 3 shows the markers on chromosome 1 that co-segregate with cell wall digestibility (NDFd) in the Stiff Stalk subpopulation at a p-level ≤0.01. X axis: distance expressed in cM on Chr. 1. Y axis: probability value.

FIG. 4 shows the markers on chromosome 1 that co-segregate with cell wall digestibility (NDFd) in the Stiff Stalk subpopulation at a p-level ≤0.001. X axis: distance expressed in cM on Chr. 1. Y axis: probability value.

FIG. 5 shows the results obtained from a candidate gene association study, in which primers were developed from a laccase-like locus, representing marker SCW_04_5b, and the marker was tested for association with cell wall digestibility (NDFd), as measured using wet chemistry, in a Stiff Stalk subpopulation. Only the informative SNP positions are shown.

FIG. 6 is a table showing the primer and reference sequence information for each of the PHM markers described herein.

The sequence descriptions and Sequence Listing attached hereto comply with the rules governing nucleotide and/or amino acid sequence disclosures in patent applications as set forth in 37 C.F.R. §1.821-1.825. The Sequence Listing contains the one letter code for nucleotide sequence characters and the three letter codes for amino acids as defined in conformity with the IUPAC-IUBMB standards described in Nucleic Acids Res. 13:3021-3030 (1985) and in the Biochemical J. 219 (2):345-373 (1984) which are herein incorporated by reference. The symbols and format used for nucleotide and amino acid sequence data comply with the rules set forth in 37 C.F.R. §1.822.

SEQ ID NO:1 is the PHM8098 reference sequence.
SEQ ID NO:2 is the PHM14801 reference sequence.
SEQ ID NO:3 is the PHM4175 reference sequence.
SEQ ID NO:4 is the PHM1783 reference sequence.
SEQ ID NO:5 is the PHM3364 reference sequence.
SEQ ID NO:6 is the PHM1730 reference sequence.
SEQ ID NO:7 is the PHM4359 reference sequence.
SEQ ID NO:8 is the PHM9167 reference sequence.
SEQ ID NO:9 is the PHM8098 forward external primer.
SEQ ID NO:10 is the PHM8098 forward internal primer.
SEQ ID NO:11 is the PHM8098 reverse internal primer.
SEQ ID NO:12 is the PHM8098 reverse external primer.
SEQ ID NO:13 is the PHM14801 forward external primer.
SEQ ID NO:14 is the PHM14801 forward internal primer.
SEQ ID NO:15 is the PHM14801 reverse internal primer.
SEQ ID NO:16 is the PHM14801 reverse external primer.
SEQ ID NO:17 is the PHM4175 forward external primer.
SEQ ID NO:18 is the PHM4175 forward internal primer.

SEQ ID NO:19 is the PHM4175 reverse internal primer.
SEQ ID NO:20 is the PHM4175 reverse external primer.
SEQ ID NO:21 is the PHM1783 forward external primer.
SEQ ID NO:22 is the PHM1783 forward internal primer.
SEQ ID NO:23 is the PHM1783 reverse internal primer.
SEQ ID NO:24 is the PHM1783 reverse external primer.
SEQ ID NO:25 is the PHM3364 forward external primer.
SEQ ID NO:26 is the PHM3364 forward internal primer.
SEQ ID NO:27 is the PHM3364 reverse internal primer.
SEQ ID NO:28 is the PHM3364 reverse external primer.
SEQ ID NO:29 is the PHM1730 forward external primer.
SEQ ID NO:30 is the PHM1730 forward internal primer.
SEQ ID NO:31 is the PHM1730 reverse internal primer.
SEQ ID NO:32 is the PHM1730 reverse external primer.
SEQ ID NO:33 is the PHM4359 forward external primer.
SEQ ID NO:34 is the PHM4359 forward internal primer.
SEQ ID NO:35 is the PHM4359 reverse internal primer.
SEQ ID NO:36 is the PHM4359 reverse external primer.
SEQ ID NO:37 is the PHM9167 forward external primer.
SEQ ID NO:38 is the PHM9167 forward internal primer.
SEQ ID NO:39 is the PHM9167 reverse internal primer.
SEQ ID NO:40 is the PHM9167 reverse external primer.
SEQ ID NO:41 is the nucleotide sequence of the *Zea mays* laccase-like polynucleotide ORF.
SEQ ID NO:42 is the amino acid sequence of the *Zea mays* laccase-like polypeptide.
SEQ ID NO:43 is the nucleotide sequence of the *Zea mays* laccase-like polynucleotide transcript.
SEQ ID NO:44 is the amino acid sequence of the *Zea mays* "unknown" protein (NCBI GI No: 194692196).
SEQ ID NO:45 is the amino acid sequence of the *Oryza sativa* laccase protein (NCBI GI No: 115452197).
SEQ ID NO:46 is the SCW_04_5b reverse primer.
SEQ ID NO:47 is the SCW_04_5b forward primer.
SEQ ID NO:48 is the SCW_04_5b reference sequence.
SEQ ID NO:49 is the genomic sequence comprising the SCW_04_5b locus and the laccase-like gene (SEQ ID NO:41).
SEQ ID NO:50 is the PHM13936 forward external primer.
SEQ ID NO:51 is the PHM13936 forward internal primer.
SEQ ID NO:52 is the PHM13936 reverse internal primer.
SEQ ID NO:53 is the PHM13936 reverse external primer.
SEQ ID NO:54 is the PHM15671 forward external primer.
SEQ ID NO:55 is the PHM15671 forward internal primer.
SEQ ID NO:56 is the PHM15671 reverse internal primer.
SEQ ID NO:57 is the PHM15671 reverse external primer.
SEQ ID NO:58 is the PHM14875 forward external primer.
SEQ ID NO:59 is the PHM14875 forward internal primer.
SEQ ID NO:60 is the PHM14875 reverse internal primer.
SEQ ID NO:61 is the PHM14875 reverse external primer.
SEQ ID NO:62 is the PHM11079 forward external primer.
SEQ ID NO:63 is the PHM11079 forward internal primer.
SEQ ID NO:64 is the PHM11079 reverse internal primer.
SEQ ID NO:65 is the PHM11079 reverse external primer.
SEQ ID NO:66 is the PHM15150 forward external primer.
SEQ ID NO:67 is the PHM15150 forward internal primer.
SEQ ID NO:68 is the PHM15150 reverse internal primer.
SEQ ID NO:69 is the PHM15150 reverse external primer.
SEQ ID NO:70 is the PHM1239 forward external primer.
SEQ ID NO:71 is the PHM1239 forward internal primer.
SEQ ID NO:72 is the PHM1239 reverse internal primer.
SEQ ID NO:73 is the PHM1239 reverse external primer.
SEQ ID NO:74 is the PHM9528 forward external primer.
SEQ ID NO:75 is the PHM9528 forward internal primer.
SEQ ID NO:76 is the PHM9528 reverse internal primer.
SEQ ID NO:77 is the PHM9528 reverse external primer.
SEQ ID NO:78 is the PHM14541 forward external primer.
SEQ ID NO:79 is the PHM14541 forward internal primer.
SEQ ID NO:80 is the PHM14541 reverse internal primer.
SEQ ID NO:81 is the PHM14541 reverse external primer
SEQ ID NO:82 is the PHM2690 forward external primer.
SEQ ID NO:83 is the PHM2690 forward internal primer.
SEQ ID NO:84 is the PHM2690 reverse internal primer.
SEQ ID NO:85 is the PHM2690 reverse external primer.
SEQ ID NO:86 is the PHM1241 forward external primer.
SEQ ID NO:87 is the PHM1241 forward internal primer.
SEQ ID NO:88 is the PHM1241 reverse internal primer.
SEQ ID NO:89 is the PHM1241 reverse external primer.
SEQ ID NO:90 is the PHM11733 forward external primer.
SEQ ID NO:91 is the PHM11733 forward internal primer.
SEQ ID NO:92 is the PHM11733 reverse internal primer.
SEQ ID NO:93 is the PHM11733 reverse external primer.
SEQ ID NO:94 is the PHM13936 reference sequence.
SEQ ID NO:95 is the PHM15671 reference sequence.
SEQ ID NO:96 is the PHM14875 reference sequence.
SEQ ID NO:97 is the PHM11079 reference sequence.
SEQ ID NO:98 is the PHM15150 reference sequence.
SEQ ID NO:99 is the PHM1239 reference sequence.
SEQ ID NO:100 is the PHM9528 reference sequence.
SEQ ID NO:101 is the PHM14541 reference sequence.
SEQ ID NO:102 is the PHM2690 reference sequence.
SEQ ID NO:103 is the PHM1241 reference sequence.
SEQ ID NO:104 is the PHM11733 reference sequence

DETAILED DESCRIPTION

The present invention provides allelic compositions in maize and methods for identifying and selecting maize plants with increased cell wall digestibility. The following definitions are provided as an aid to understand this invention.

The term "allele" refers to one of two or more different nucleotide sequences that occur at a specific locus.

An "amplicon" is an amplified nucleic acid, e.g., a nucleic acid that is produced by amplifying a template nucleic acid by any available amplification method (e.g., PCR, LCR, transcription, or the like).

The term "amplifying" in the context of nucleic acid amplification is any process whereby additional copies of a selected nucleic acid (or a transcribed form thereof) are produced. Typical amplification methods include various polymerase based replication methods, including the polymerase chain reaction (PCR), ligase mediated methods such as the ligase chain reaction (LCR) and RNA polymerase based amplification (e.g., by transcription) methods.

The term "assemble" applies to BACs and their propensities for coming together to form contiguous stretches of DNA. A BAC "assembles" to a contig based on sequence alignment, if the BAC is sequenced, or via the alignment of its BAC fingerprint to the fingerprints of other BACs. The assemblies can be found using the Maize Genome Browser, which is publicly available on the internet.

An allele is "associated with" a trait when it is linked to it and when the presence of the allele is an indicator that the desired trait or trait form will occur in a plant comprising the allele.

A "BAC", or bacterial artificial chromosome, is a cloning vector derived from the naturally occurring F factor of *Escherichia coli*. BACs can accept large inserts of DNA sequence. In maize, a number of BACs, or bacterial artificial chromosomes, each containing a large insert of maize genomic DNA, have been assembled into contigs (overlapping contiguous genetic fragments, or "contiguous DNA").

"Backcrossing" refers to the process whereby hybrid progeny are repeatedly crossed back to one of the parents. In a backcrossing scheme, the "donor" parent refers to the parental plant with the desired gene or locus to be introgressed. The "recipient" parent (used one or more times) or "recurrent" parent (used two or more times) refers to the parental plant into which the gene or locus is being introgressed. For example, see Ragot, M. et al. (1995) Marker-assisted backcrossing: a practical example, in *Techniques et Utilisations des Marqueurs Moleculaires Les Colloques*, Vol. 72, pp. 45-56, and Openshaw et al., (1994) *Marker-assisted Selection in Backcross Breeding, Analysis of Molecular Marker Data*, pp. 41-43. The initial cross gives rise to the F1 generation; the term "BC1" then refers to the second use of the recurrent parent, "BC2" refers to the third use of the recurrent parent, and so on.

A plant "cell wall" is a highly heterogeneous and complex structure consisting of cellulose microfibrils embedded in a matrix of hemicellulose, pectin (only trace amounts in grasses), cell wall proteins, and phenolic compounds such as lignin.

"Cell wall digestibility" refers to the degree to which cell wall polysaccharides are hydrolyzed by microorganisms or hydrolytic enzymes into simple sugars. Wall polysaccharides must be broken down into simple sugars for digestion by livestock or for conversion into ethanol by fermenting yeast or microorganisms. Plants with "increased cell wall digestibility" have cell walls that are more digestible, whereas plants with "decreased cell wall digestibility" have cell walls that are less digestible.

A centimorgan ("cM") is a unit of measure of recombination frequency. One cM is equal to a 1% chance that a marker at one genetic locus will be separated from a marker at a second locus due to crossing over in a single generation.

As used herein, the term "chromosomal interval" designates a contiguous linear span of genomic DNA that resides in planta on a single chromosome. The genetic elements or genes located on a single chromosomal interval are physically linked. The size of a chromosomal interval is not particularly limited. In some aspects, the genetic elements located within a single chromosomal interval are genetically linked, typically with a genetic recombination distance of, for example, less than or equal to 20 cM, or alternatively, less than or equal to 10 cM. That is, two genetic elements within a single chromosomal interval undergo recombination at a frequency of less than or equal to 20% or 10%.

The term "chromosomal interval" designates any and all intervals defined by any of the markers set forth in this invention. A chromosomal interval that correlates with cell wall digestibility is provided. This interval, located on chromosome 1, comprises and is flanked by PHM13936 and PHM11733. A subinterval of chromosomal interval PHM13936 and PHM11733 is PHM8098 and PHM9167.

The term "complement" refers to a nucleotide sequence that is complementary to a given nucleotide sequence, i.e. the sequences are related by the base-pairing rules.

The term "contiguous DNA" refers to overlapping contiguous genetic fragments.

The term "crossed" or "cross" means the fusion of gametes via pollination to produce progeny (e.g., cells, seeds or plants). The term encompasses both sexual crosses (the pollination of one plant by another) and selfing (self-pollination, e.g., when the pollen and ovule are from the same plant). The term "crossing" refers to the act of fusing gametes via pollination to produce progeny.

A "favorable allele" is the allele at a particular locus that confers, or contributes to, a desirable phenotype, e.g., increased cell wall digestibility, or alternatively, is an allele that allows the identification of plants with decreased cell wall digestibility that can be removed from a breeding program or planting ("counterselection"). A favorable allele of a marker is a marker allele that segregates with the favorable phenotype, or alternatively, segregates with the unfavorable plant phenotype, therefore providing the benefit of identifying plants.

"Fragment" is intended to mean a portion of a nucleotide sequence. Fragments can be used as hybridization probes or PCR primers using methods disclosed herein.

A "genetic map" is a description of genetic linkage relationships among loci on one or more chromosomes (or chromosomes) within a given species, generally depicted in a diagrammatic or tabular form. For each genetic map, distances between loci are measured by the recombination frequencies between them, and recombinations between loci can be detected using a variety of molecular genetic markers (also called molecular markers). A genetic map is a product of the mapping population, types of markers used, and the polymorphic potential of each marker between different populations. The order and genetic distances between loci can differ from one genetic map to another. For example, 10 cM on the internally derived genetic map (also referred to herein as "PHB" for Pioneer Hi-Bred) is roughly equivalent to 25-30 cM on the IBM2 2005 neighbors frame map (a high resolution map available on maizeGDB). However, information can be correlated from one map to another using a general framework of common markers. One of ordinary skill in the art can use the framework of common markers to identify the positions of markers and other loci of interest on each individual genetic map. A comparison of marker positions between the internally derived genetic map and the IBM2 neighbors genetic map can be seen in Table 2A.

The term "Genetic Marker" shall refer to any type of nucleic acid based marker, including but not limited to, Restriction Fragment Length Polymorphism (RFLP), Simple Sequence Repeat (SSR), Random Amplified Polymorphic DNA (RAPD), Cleaved Amplified Polymorphic Sequences (CAPS) (Rafalski and Tingey, 1993, *Trends in Genetics* 9:275-280), Amplified Fragment Length Polymorphism (AFLP) (Vos et al, 1995, *Nucleic Acids Res.* 23:4407-4414), Single Nucleotide Polymorphism (SNP) (Brookes, 1999, *Gene* 234:177-186), Sequence Characterized Amplified Region (SCAR) (Paran and Michelmore, 1993, *Theor. Appl. Genet.* 85:985-993), Sequence Tagged Site (STS) (Onozaki et al., 2004, *Euphytica* 138:255-262), Single Stranded Conformation Polymorphism (SSCP) (Orita et al., 1989, *Proc Natl Acad Sci USA* 86:2766-2770), Inter-Simple Sequence Repeat (ISSR) (Blair et al., 1999, *Theor. Appl. Genet.* 98:780-792), Inter-Retrotransposon Amplified Polymorphism (IRAP), Retrotransposon-Microsatellite Amplified Polymorphism (REMAP) (Kalendar et al., 1999, *Theor. Appl. Genet.* 98:704-711), an RNA cleavage product (such as a Lynx tag), and the like.

"Genetic recombination frequency" is the frequency of a crossing over event (recombination) between two genetic loci. Recombination frequency can be observed by following the segregation of markers and/or traits following meiosis.

"Genome" refers to the total DNA, or the entire set of genes, carried by a chromosome or chromosome set.

The term "genotype" is the genetic constitution of an individual (or group of individuals) at one or more genetic loci, as contrasted with the observable trait (the phenotype). Genotype is defined by the allele(s) of one or more known loci that the individual has inherited from its parents. The term genotype can be used to refer to an individual's genetic constitution at a single locus, at multiple loci, or, more generally, the term genotype can be used to refer to an individual's genetic make-up for all the genes in its genome.

"Germplasm" refers to genetic material of or from an individual (e.g., a plant line, a group of individuals (e.g., a plant line, variety or family), or a clone derived from a line, variety, species, or culture. The germplasm can be part of an organism or cell, or can be separate from the organism or cell. In general, germplasm provides genetic material with a specific molecular makeup that provides a physical foundation for some or all of the hereditary qualities of an organism or cell culture. As used herein, germplasm includes cells, seed or tissues from which new plants may be grown, or plant parts, such as leafs, stems, pollen, or cells that can be cultured into a whole plant.

A "haplotype" is the genotype of an individual at a plurality of genetic loci, i.e. a combination of alleles. Typically, the genetic loci described by a haplotype are physically and genetically linked, i.e., on the same chromosome segment. The term "haplotype" can refer to sequence polymorphisms at a particular locus, such as a single marker locus, or sequence polymorphisms at multiple loci along a chromosomal segment in a given genome. The former can also be referred to as "marker haplotypes" or "marker alleles", while the latter can be referred to as "long-range haplotypes".

A "heterotic group" comprises a set of genotypes that perform well when crossed with genotypes from a different heterotic group (Hallauer et al. (1998) Corn breeding, p. 463-564. In G. F. Sprague and J. W. Dudley (ed.) *Corn and corn improvement*). Inbred lines are classified into heterotic groups, and are further subdivided into families within a heterotic group, based on several criteria such as pedigree, molecular marker-based associations, and performance in hybrid combinations (Smith et al. (1990) *Theor. Appl. Gen.* 80:833-840). The two most widely used heterotic groups in the United States are referred to as "Iowa Stiff Stalk Synthetic" (BSSS) and "Lancaster" or "Lancaster Sure Crop" (sometimes referred to as NSS, or non-Stiff Stalk).

The term "heterozygous" means a genetic condition wherein different alleles reside at corresponding loci on homologous chromosomes.

The term "homozygous" means a genetic condition wherein identical alleles reside at corresponding loci on homologous chromosomes.

"Hybridization" or "nucleic acid hybridization" refers to the pairing of complementary RNA and DNA strands as well as the pairing of complementary DNA single strands.

The term "hybridize" means to form base pairs between complementary regions of nucleic acid strands.

An "IBM genetic map" refers to any of following maps: IBM, IBM2, IBM2 neighbors, IBM2 FPC0507, IBM2 2004 neighbors, IBM2 2005 neighbors, or IBM2 2005 neighbors frame. IBM genetic maps are based on a B73×Mo17 population in which the progeny from the initial cross were randommated for multiple generations prior to constructing recombinant inbred lines for mapping. Newer versions reflect the addition of genetic and BAC mapped loci as well as enhanced map refinement due to the incorporation of information obtained from other genetic maps.

The term "indel" refers to an insertion or deletion, wherein one line may be referred to as having an insertion relative to a second line, or the second line may be referred to as having a deletion relative to the first line.

The term "introgression" or "introgressing" refers to the transmission of a desired allele of a genetic locus from one genetic background to another. For example, introgression of a desired allele at a specified locus can be transmitted to at least one progeny via a sexual cross between two parents of the same species, where at least one of the parents has the desired allele in its genome. Alternatively, for example, transmission of an allele can occur by recombination between two donor genomes, e.g., in a fused protoplast, where at least one of the donor protoplasts has the desired allele in its genome. The desired allele can be, e.g., a selected allele of a marker, a QTL, a transgene, or the like. In any case, offspring comprising the desired allele can be repeatedly backcrossed to a line having a desired genetic background and selected for the desired allele, to result in the allele becoming fixed in a selected genetic background. For example, the chromosome 1 locus described herein may be introgressed into a recurrent parent that has decreased cell wall digestibility. The recurrent parent line with the introgressed gene or locus then has increased cell wall digestibility.

The process of "introgressing" is often referred to as "backcrossing" when the process is repeated two or more times.

As used herein, the term "linkage" is used to describe the degree with which one marker locus is associated with another marker locus or some other locus (for example, a cell wall digestibility locus). The linkage relationship between a molecular marker and a phenotype is given as a "probability" or "adjusted probability". Linkage can be expressed as a desired limit or range. For example, in some embodiments, any marker is linked (genetically and physically) to any other marker when the markers are separated by less than 50, 40, 30, 25, 20, or 15 map units (or cM). In some aspects, it is advantageous to define a bracketed range of linkage, for example, between 10 and 20 cM, between 10 and 30 cM, or between 10 and 40 cM. The more closely a marker is linked to a second locus, the better an indicator for the second locus that marker becomes. Thus, "closely linked loci" such as a marker locus and a second locus display an inter-locus recombination frequency of 10% or less, preferably about 9% or less, still more preferably about 8% or less, yet more preferably about 7% or less, still more preferably about 6% or less, yet more preferably about 5% or less, still more preferably about 4% or less, yet more preferably about 3% or less, and still more preferably about 2% or less. In highly preferred embodiments, the relevant loci display a recombination frequency of about 1% or less, e.g., about 0.75% or less, more preferably about 0.5% or less, or yet more preferably about 0.25% or less. Two loci that are localized to the same chromosome, and at such a distance that recombination between the two loci occurs at a frequency of less than 10% (e.g., about 9%, 8%, 7%, 6%, 5%, 4%, 3%, 2%, 1%, 0.75%, 0.5%, 0.25%, or less) are also said to be "proximal to" each other. Since one cM is the distance between two markers that show a 1% recombination frequency, any marker is closely linked (genetically and physically) to any other marker that is in close proximity, e.g., at or less than 10 cM distant. Two closely linked markers on the same chromosome can be positioned 9, 8, 7, 6, 5, 4, 3, 2, 1, 0.75, 0.5 or 0.25 cM or less from each other.

The term "linkage disequilibrium" refers to a non-random segregation of genetic loci or traits (or both). In either case, linkage disequilibrium implies that the relevant loci are within sufficient physical proximity along a length of a chromosome so that they segregate together with greater than random (i.e., non-random) frequency (in the case of co-segregating traits, the loci that underlie the traits are in sufficient proximity to each other). Markers that show linkage disequilibrium are considered linked. Linked loci co-segregate more than 50% of the time, e.g., from about 51% to about 100% of the time. In other words, two markers that co-segregate have a recombination frequency of less than 50% (and by definition, are separated by less than 50 cM on the same chromosome.) As used herein, linkage can be between two markers, or alternatively between a marker and a phenotype. A marker locus can be "associated with" (linked to) a trait, e.g., increased cell wall digestibility. The degree of linkage of a molecular marker to a phenotypic trait is measured, e.g., as a statistical probability of co-segregation of that molecular marker with the phenotype.

Linkage disequilibrium is most commonly assessed using the measure $r^2$, which is calculated using the formula described by Hill, W. G. and Robertson, A, *Theor. Appl. Genet.* 38:226-231(1968). When $r^2=1$, complete LD exists between the two marker loci, meaning that the markers have not been separated by recombination and have the same allele frequency. Values for $r^2$ above ⅓ indicate sufficiently strong LD to be useful for mapping (Ardlie et al., *Nature Reviews Genetics* 3:299-309 (2002)). Hence, alleles are in linkage disequilibrium when $r^2$ values between pairwise marker loci are greater than or equal to 0.33, 0.4, 0.5, 0.6, 0.7, 0.8, 0.9, or 1.0.

As used herein, "linkage equilibrium" describes a situation where two markers independently segregate, i.e., sort among progeny randomly. Markers that show linkage equilibrium are considered unlinked (whether or not they lie on the same chromosome).

The "logarithm of odds (LOD) value" or "LOD score" (Risch, Science 255:803-804 (1992)) is used in interval mapping to describe the degree of linkage between two marker loci. A LOD score of three between two markers indicates that linkage is 1000 times more likely than no linkage, while a LOD score of two indicates that linkage is 100 times more likely than no linkage. LOD scores greater than or equal to two may be used to detect linkage.

A "locus" is a position on a chromosome where a gene or marker is located.

"Maize" refers to a plant of the *Zea mays* L. ssp. *mays* and is also known as "corn".

The term "maize plant" includes: whole maize plants, maize plant cells, maize plant protoplast, maize plant cell or maize tissue cultures from which maize plants can be regenerated, maize plant calli, and maize plant cells that are intact in maize plants or parts of maize plants, such as maize seeds, maize cobs, maize flowers, maize cotyledons, maize leaves, maize stems, maize buds, maize roots, maize root tips, and the like.

A "marker" is a nucleotide sequence or encoded product thereof (e.g., a protein) used as a point of reference. For markers to be useful at detecting recombinations, they need to detect differences, or polymorphisms, within the population being monitored. For molecular markers, this means differences at the DNA level due to polynucleotide sequence differences (e.g. SSRs, RFLPs, FLPs, SNPs). The genomic variability can be of any origin, for example, insertions, deletions, duplications, repetitive elements, point mutations, recombination events, or the presence and sequence of transposable elements. Molecular markers can be derived from genomic or expressed nucleic acids (e.g., ESTs) and can also refer to nucleic acids used as probes or primer pairs capable of amplifying sequence fragments via the use of PCR-based methods. A large number of maize molecular markers are known in the art, and are published or available from various sources, such as the Maize GDB internet resource and the Arizona Genomics Institute internet resource run by the University of Arizona.

Markers corresponding to genetic polymorphisms between members of a population can be detected by methods well-established in the art. These include, e.g., DNA sequencing, PCR-based sequence specific amplification methods, detection of restriction fragment length polymorphisms (RFLP), detection of isozyme markers, detection of polynucleotide polymorphisms by allele specific hybridization (ASH), detection of amplified variable sequences of the plant genome, detection of self-sustained sequence replication, detection of simple sequence repeats (SSRs), detection of single nucleotide polymorphisms (SNPs), or detection of amplified fragment length polymorphisms (AFLPs). Well established methods are also known for the detection of expressed sequence tags (ESTs) and SSR markers derived from EST sequences and randomly amplified polymorphic DNA (RAPD).

A "marker allele", alternatively an "allele of a marker locus", can refer to one of a plurality of polymorphic nucleotide sequences found at a marker locus in a population that is polymorphic for the marker locus.

"Marker assisted selection" (of MAS) is a process by which phenotypes are selected based on marker genotypes.

"Marker assisted counter-selection" is a process by which marker genotypes are used to identify plants that will not be selected, allowing them to be removed from a breeding program or planting.

A "marker haplotype" refers to a combination of alleles at a marker locus, e.g. PHM1730 allele 2.

A "marker locus" is a specific chromosome location in the genome of a species where a specific marker can be found. A marker locus can be used to track the presence of a second linked locus, e.g., a linked locus that encodes or contributes to expression of a phenotypic trait. For example, a marker locus can be used to monitor segregation of alleles at a locus, such as a QTL or single gene, that are genetically or physically linked to the marker locus.

A "marker probe" is a nucleic acid sequence or molecule that can be used to identify the presence of a marker locus, e.g., a nucleic acid probe that is complementary to a marker locus sequence, through nucleic acid hybridization. Marker probes comprising 30 or more contiguous nucleotides of the marker locus ("all or a portion" of the marker locus sequence) may be used for nucleic acid hybridization. Alternatively, in some aspects, a marker probe refers to a probe of any type that is able to distinguish (i.e., genotype) the particular allele that is present at a marker locus.

The term "molecular marker" may be used to refer to a genetic marker, as defined above, or an encoded product thereof (e.g., a protein) used as a point of reference when identifying a linked locus. A marker can be derived from genomic nucleotide sequences or from expressed nucleotide sequences (e.g., from a spliced RNA, a cDNA, etc.), or from an encoded polypeptide. The term also refers to nucleic acid sequences complementary to or flanking the marker sequences, such as nucleic acids used as probes or primer pairs capable of amplifying the marker sequence. A "molecular marker probe" is a nucleic acid sequence or molecule that can be used to identify the presence of a marker locus, e.g., a nucleic acid probe that is complementary to a marker locus sequence. Alternatively, in some aspects, a marker probe refers to a probe of any type that is able to distinguish (i.e., genotype) the particular allele that is present at a marker locus. Nucleic acids are "complementary" when they specifically hybridize in solution, e.g., according to Watson-Crick base pairing rules. Some of the markers described herein are also referred to as hybridization markers when located on an indel region, such as the non-collinear region described herein. This is because the insertion region is, by definition, a polymorphism vis a vis a plant without the insertion. Thus, the marker need only indicate whether the indel region is present or absent. Any suitable marker detection technology may be used to identify such a hybridization marker, e.g. SNP technology is used in the examples provided herein.

"NDFd" stands for NDF digestibility, or "neutral detergent fiber digestibility". NDFd is the portion of NDF that is digested in the rumen.

"Nucleotide sequence", "polynucleotide", "nucleic acid sequence", and "nucleic acid fragment" are used interchangeably and refer to a polymer of RNA or DNA that is single- or double-stranded, optionally containing synthetic, non-natural or altered nucleotide bases. A "nucleotide" is a monomeric unit from which DNA or RNA polymers are constructed, and consists of a purine or pyrimidine base, a pentose, and a phosphoric acid group. Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

The terms "phenotype", or "phenotypic trait" or "trait" refers to one or more traits of an organism. The phenotype can be observable to the naked eye, or by any other means of evaluation known in the art, e.g., microscopy, biochemical analysis, or an electromechanical assay. In some cases, a phenotype is directly controlled by a single gene or genetic locus, i.e., a "single gene trait". In other cases, a phenotype is the result of several genes.

Each "PHM" marker represents two sets of primers (external and internal) that when used in a nested PCR, amplify a specific piece of DNA. The external set is used in the first round of PCR, after which the internal sequences are used for a second round of PCR on the products of the first round. This increases the specificity of the reaction. The annealing temperature for all the primers listed in FIG. 6 is 55° C. SNP markers can also be developed for specific polymorphisms identified using the PHM markers.

A "physical map" of the genome is a map showing the linear order of identifiable landmarks (including genes, markers, etc.) on chromosome DNA. However, in contrast to genetic maps, the distances between landmarks are absolute (for example, measured in base pairs or isolated and overlapping contiguous genetic fragments) and not based on genetic recombination.

A "plant" can be a whole plant, any part thereof, or a cell or tissue culture derived from a plant. Thus, the term "plant" can refer to any of: whole plants, plant components or organs (e.g., leaves, stems, roots, etc.), plant tissues, seeds, plant cells, and/or progeny of the same. A plant cell is a cell of a plant, taken from a plant, or derived through culture from a cell taken from a plant.

A "polymorphism" is a variation in the DNA that is too common to be due merely to new mutation. A polymorphism must have a frequency of at least 1% in a population. A polymorphism can be a single nucleotide polymorphism, or SNP, or an insertion/deletion polymorphism, also referred to herein as an "indel".

The "probability value" or "p-value" is the statistical likelihood that the particular combination of a phenotype and the presence or absence of a particular marker allele is random. Thus, the lower the probability score, the greater the likelihood that a phenotype and a particular marker will co-segregate. In some aspects, the probability score is considered "significant" or "nonsignificant". In some embodiments, a probability score of 0.05 (p=0.05, or a 5% probability) of random assortment is considered a significant indication of co-segregation. However, an acceptable probability can be any probability of less than 50% (p=0.5). For example, a significant probability can be less than 0.25, less than 0.20, less than 0.15, less than 0.1, less than 0.05, less than 0.01, or less than 0.001.

The term "progeny" refers to the offspring generated from a cross.

A "progeny plant" is generated from a cross between two plants.

A "reference sequence" is a defined sequence used as a basis for sequence comparison. The reference sequence is obtained by genotyping a number of lines at the locus, aligning the nucleotide sequences in a sequence alignment program (e.g. Sequencher), and then obtaining the consensus sequence of the alignment.

The "Stiff Stalk" heterotic group represents a major heterotic group in the northern U.S. and Canadian corn growing regions. It can also be referred to as the Iowa Stiff Stalk Synthetic (or BSSS) heterotic group.

A "topcross test" is a progeny test derived by crossing each parent with the same tester, usually a homozygous line. The parent being tested can be an open-pollinated variety, a cross, or an inbred line.

The phrase "under stringent conditions" refers to conditions under which a probe or polynucleotide will hybridize to a specific nucleic acid sequence, typically in a complex mixture of nucleic acids, but to essentially no other sequences. Stringent conditions are sequence-dependent and will be different in different circumstances.

Longer sequences hybridize specifically at higher temperatures. Generally, stringent conditions are selected to be about 5-10° C. lower than the thermal melting point (Tm) for the specific sequence at a defined ionic strength pH. The Tm is the temperature (under defined ionic strength, pH, and nucleic acid concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3, and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, preferably 10 times background hybridization. Exemplary stringent hybridization conditions are often: 50% formamide, 5×SSC, and 1% SDS, incubating at 42° C., or, 5×SSC, 1% SDS, incubating at 65° C., with wash in 0.2×SSC, and 0.1% SDS at 65° C. For PCR, a temperature of about 36° C. is typical for low stringency amplification, although annealing temperatures may vary between about 32° C. and 48° C., depending on primer length. Additional guidelines for determining hybridization parameters are provided in numerous references.

Sequence alignments and percent identity calculations may be determined using a variety of comparison methods designed to detect homologous sequences including, but not limited to, the MEGALIGN® program of the LASERGENE® bioinformatics computing suite (DNASTAR® Inc., Madison, Wis.). Unless stated otherwise, multiple alignment of the sequences provided herein were performed using the Clustal V method of alignment (Higgins and Sharp, *CABIOS*. 5:151-153 (1989)) with the default parameters (GAP PENALTY=10, GAP LENGTH PENALTY=10). Default parameters for pairwise alignments and calculation of percent identity of protein sequences using the Clustal V method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences, using the Clustal V program, it is possible to obtain "percent identity" and "divergence" values by viewing the "sequence distances" table on the same program; unless stated otherwise, percent identities and divergences provided and claimed herein were calculated in this manner.

Before describing the present invention in detail, it should be understood that this invention is not limited to particular embodiments. It also should be understood that the terminology used herein is for the purpose of describing particular embodiments, and is not intended to be limiting. As used herein and in the appended claims, terms in the singular and the singular forms "a", "an" and "the", for example, include plural referents unless the content clearly dictates otherwise. Thus, for example, reference to "plant", "the plant" or "a plant" also includes a plurality of plants. Depending on the context, use of the term "plant" can also include genetically similar or identical progeny of that plant. The use of the term "a nucleic acid" optionally includes many copies of that nucleic acid molecule.

Genetic Mapping

It has been recognized for quite some time that specific genetic loci correlating with particular phenotypes, such as cell wall digestibility, can be mapped in an organism's genome. The plant breeder can advantageously use molecular markers to identify desired individuals by detecting marker alleles that show a statistically significant probability of co-segregation with a desired phenotype, manifested as linkage disequilibrium. By identifying a molecular marker or clusters of molecular markers that co-segregate with a trait of interest, the breeder is able to rapidly select a desired phenotype by selecting for the proper molecular marker allele (a process called marker-assisted selection, or MAS).

A variety of methods well known in the art are available for detecting molecular markers or clusters of molecular markers that co-segregate with a trait of interest, such as cell wall digestibility. The basic idea underlying these methods is the detection of markers, for which alternative genotypes (or alleles) have significantly different average phenotypes. Thus, one makes a comparison among marker loci of the magnitude of difference among alternative genotypes (or alleles) or the level of significance of that difference. Trait genes are inferred to be located nearest the marker(s) that have the greatest associated genotypic difference.

Two such methods used to detect trait loci of interest are: 1) Population-based association analysis and 2) Traditional linkage analysis. In a population-based association analysis, lines are obtained from pre-existing populations with multiple founders, e.g. elite breeding lines. Population-based association analyses rely on the decay of linkage disequilibrium (LD) and the idea that in an unstructured population, only correlations between genes controlling a trait of interest and markers closely linked to those genes will remain after so many generations of random mating. In reality, most pre-existing populations have population substructure. Thus, the use of a structured association approach helps to control population structure by allocating individuals to populations using data obtained from markers randomly distributed across the genome, thereby minimizing disequilibrium due to population structure within the individual populations (also called subpopulations). The phenotypic values are compared to the genotypes (alleles) at each marker locus for each line in the subpopulation. A significant marker-trait association indicates the close proximity between the marker locus and one or more genetic loci that are involved in the expression of that trait.

The same principles underlie traditional linkage analysis; however, LD is generated by creating a population from a small number of founders. The founders are selected to maximize the level of polymorphism within the constructed population, and polymorphic sites are assessed for their level of cosegregation with a given phenotype. A number of statistical methods have been used to identify significant marker-trait associations. One such method is an interval mapping approach (Lander and Botstein, *Genetics* 121:185-199 (1989), in which each of many positions along a genetic map (say at 1 cM intervals) is tested for the likelihood that a gene controlling a trait of interest is located at that position. The genotype/phenotype data are used to calculate for each test position a LOD score (log of likelihood ratio). When the LOD score exceeds a threshold value, there is significant evidence for the location of a gene controlling the trait of interest at that position on the genetic map (which will fall between two particular marker loci).

Markers Associated with Cell Wall Digestibility

Markers associated with cell wall digestibility are identified herein. The methods involve detecting the presence of at least one marker allele associated with the enhanced resistance in the germplasm of a maize plant. The marker locus can be selected from any of the marker loci provided in Table 1, including PHM8098, PHM14801, PHM4175, PHM1783, PHM3364, PHM1730, PHM4359, and PHM9167; SCW_04_5b; and any other marker linked to these markers (linked markers can be determined from the MaizeGDB resource; see framework of markers in Table 2A). The marker locus can be selected from any of the marker loci provided in Table 1, including PHM13936, PHM15671, PHM14875, PHM11079, PHM15150, PHM1239, PHM9528, PHM14541, PHM2690, PHM1241, and PHM11733, and any other marker linked to these markers (linked markers can be determined from the MaizeGDB resource; see framework of markers in Table 2A).

The genetic elements or genes located on a contiguous linear span of genomic DNA on a single chromosome are physically linked. PHM13936 and PHM11733, both highly associated with cell wall digestibility (NDFd), as measured with wet chemistry, at a p-value ≤0.01, delineate a cell wall digestibility QTL on the maize physical map (FIG. 1 and FIG. 3). Any polynucleotide that assembles to the contiguous DNA between and including SEQ ID NO:94 (the reference sequence for PHM13936), or a nucleotide sequence that is 95% identical to SEQ ID NO:94 based on the Clustal V method of alignment, and SEQ ID NO:104 (the reference sequence for PHM11733), or a nucleotide sequence that is 95% identical to SEQ ID NO:104 based on the Clustal V method of alignment, can house marker loci that are associated with cell wall digestibility. FIG. 1 shows the physical map arrangement of the sequenced BACs that make up the contiguous stretch of DNA between and including PHM13936 and PHM11733. The gaps (represented by dotted lines) are not gaps in the contiguous stretch of DNA per se but are areas where BACs that have not been sequenced assemble to the physical map.

The genetic elements or genes located on a contiguous linear span of genomic DNA on a single chromosome are physically linked for the subinterval of PHM8098 and PHM9167. PHM8098 and PHM9167, both highly associated with cell wall digestibility (NDFd), as measured with wet chemistry, at a p-value ≤0.001, delineate a cell wall digestibility QTL on the maize physical map (FIG. 1). Any polynucleotide that assembles to the contiguous DNA between and including SEQ ID NO:1 (the reference sequence for PHM8098), or a nucleotide sequence that is 95% identical to SEQ ID NO:1 based on the Clustal V method of alignment, and SEQ ID NO:8 (the reference sequence for PHM9167), or a nucleotide sequence that is 95% identical to SEQ ID NO:8 based on the Clustal V method of alignment, can house marker loci that are associated with cell wall digestibility. FIG. 1 shows the physical map arrangement of the sequenced BACs that make up the contiguous stretch of DNA between and including the subinterval PHM8098 and PHM9167. The gaps (represented by dotted lines) are not gaps in the contiguous stretch of DNA per se but are areas where BACs that have not been sequenced assemble to the physical map.

A common measure of linkage is the frequency with which traits cosegregate. This can be expressed as a percentage of cosegregation (recombination frequency) or in centiMorgans (cM). The cM is a unit of measure of genetic recombination frequency. One cM is equal to a 1% chance that a trait at one genetic locus will be separated from a trait at another locus due to crossing over in a single generation (meaning the traits segregate together 99% of the time). Because chromosomal distance is approximately proportional to the frequency of crossing over events between traits, there is an approximate physical distance that correlates with recombination frequency.

Marker loci are themselves traits and can be assessed according to standard linkage analysis by tracking the marker loci during segregation. Thus, one cM is equal to a 1% chance that a marker locus will be separated from another locus, due to crossing over in a single generation.

Other markers linked to the markers listed in Table 1 can be used to predict cell wall digestibility in a maize plant. This includes any marker within 50 cM of PHM8098, PHM14801, PHM4175, PHM1783, PHM3364, PHM1730, PHM4359, SCW_04_5b, PHM9167, PHM13936, PHM15671, PHM14875, PHM11079, PHM15150, PHM1239, PHM9528, PHM14541, PHM2690, PHM1241 or PHM11733, the markers associated with the cell wall digestibility at a p-level ≤0.01 in the association analysis. The closer a marker is to a gene controlling a trait of interest, the more effective and advantageous that marker is as an indicator for the desired trait. Closely linked loci display an inter-locus cross-over frequency of about 10% or less, preferably about 9% or less, still more preferably about 8% or less, yet more preferably about 7% or less, still more preferably about 6% or less, yet more preferably about 5% or less, still more preferably about 4% or less, yet more preferably about 3% or less, and still more preferably about 2% or less. In highly preferred embodiments, the relevant loci (e.g., a marker locus and a target locus) display a recombination frequency of about 1% or less, e.g., about 0.75% or less, more preferably about 0.5% or less, or yet more preferably about 0.25% or less. Thus, the loci are about 10 cM, 9 cM, 8 cM, 7 cM, 6 cM, 5 cM, 4 cM, 3 cM, 2 cM, 1 cM, 0.75 cM, 0.5 cM or 0.25 cM or less apart. Put another way, two loci that are localized to the same chromosome, and at such a distance that recombination between the two loci occurs at a frequency of less than 10% (e.g., about 9%, 8%, 7%, 6%, 5%, 4%, 3%, 2%, 1%, 0.75%, 0.5%, 0.25%, or less) are said to be "proximal to" each other.

Although particular marker alleles can show co-segregation with increased cell wall digestibility, it is important to note that the marker locus is not necessarily responsible for the expression of the cell wall digestibility phenotype. For example, it is not a requirement that the marker polynucleotide sequence be part of a gene that imparts increased cell wall digestibility (for example, be part of the gene open reading frame). The association between a specific marker allele and the increased cell wall digestibility phenotype is due to the original "coupling" linkage phase between the marker allele and the allele in the ancestral maize line from which the allele originated. Eventually, with repeated recombination, crossing over events between the marker and genetic locus can change this orientation. For this reason, the favorable marker allele may change depending on the linkage phase that exists within the resistant parent used to create segregating populations. This does not change the fact that the marker can be used to monitor segregation of the phenotype. It only changes which marker allele is considered favorable in a given segregating population.

The term "chromosomal interval" designates any and all intervals defined by any of the markers set forth in this invention. A chromosomal interval that correlates with cell wall digestibility is provided. This interval, located on chromosome 1, comprises and is flanked by PHM13936 and PHM11733. A subinterval of chromosomal interval PHM13936 and PHM11733 is PHM8098 and PHM9167.

A variety of methods well known in the art are available for identifying chromosomal intervals. The boundaries of such chromosomal intervals are drawn to encompass markers that will be linked to the gene controlling the trait of interest. In other words, the chromosomal interval is drawn such that any marker that lies within that interval (including the terminal markers that define the boundaries of the interval) can be used as a marker for cell wall digestibility. The interval described above encompasses a cluster of markers that co-segregate with cell wall digestibility. The clustering of markers occurs in relatively small domains on the chromosomes, indicating the presence of a gene controlling the trait of interest in those chromosome regions. The interval was drawn to encompass the markers that co-segregate with cell wall digestibility. The interval encompasses markers that map within the interval as well as the markers that define the termini. For example, PHM13936 and PHM11733, separated by 14.8 cM on the internally-derived genetic map, define a chromosomal interval encompassing a cluster of markers that co-segregate with cell wall digestibility in the Stiff Stalk subpopulation at a p-level ≤0.01 (FIG. 3). A second example includes the subinterval, PHM8098 and PHM9167, separated by 3.4 cM on the internally-derived genetic map, that define a chromosomal interval encompassing a cluster of markers that co-segregate with cell wall digestibility in the Stiff Stalk subpopulation at a p-level ≤0.001 (FIG. 4). An interval described by the terminal markers that define the endpoints of the interval will include the terminal markers and any marker localizing within that chromosomal domain, whether those markers are currently known or unknown.

Chromosomal intervals can also be defined by markers that are linked to (show linkage disequilibrium with) a marker of interest, and $r^2$ is a common measure of linkage disequilibrium (LD) in the context of association studies. If the $r^2$ value of LD between any chromosome 1 marker locus lying within the interval of PHM13936 and PHM11733, the subinterval of PHM8098 and PHM9167, or any other subinterval of PHM13936 and PHM11733, and an identified marker within that interval that has an allele associated with increased cell wall digestibility is greater than ⅓ (Ardlie et al., *Nature Reviews Genetics* 3:299-309 (2002)), the loci are linked.

A marker of the invention can also be a combination of alleles at marker loci, otherwise known as a haplotype. The skilled artisan would expect that there might be additional polymorphic sites at marker loci in and around the chromosome 1 markers identified herein, wherein one or more polymorphic sites is in linkage disequilibrium (LD) with an allele associated with increased cell wall digestibility. Two particular alleles at different polymorphic sites are said to be in LD if the presence of the allele at one of the sites tends to predict the presence of the allele at the other site on the same chromosome (Stevens, *Mol. Diag.* 4:309-17 (1999)).

Marker Assisted Selection

Molecular markers can be used in a variety of plant breeding applications (e.g. see Staub et al. (1996) *Hortscience* 31: 729-741; Tanksley (1983) *Plant Molecular Biology Reporter.* 1: 3-8). One of the main areas of interest is to increase the efficiency of backcrossing and introgressing genes using marker-assisted selection (MAS). A molecular marker that demonstrates linkage with a locus affecting a desired phenotypic trait provides a useful tool for the selection of the trait in a plant population. This is particularly true where the phenotype is hard to assay, e.g. many disease resistance traits, or, occurs at a late stage in plant development, e.g. kernel characteristics. Since DNA marker assays are less laborious and take up less physical space than field phenotyping, much larger populations can be assayed, increasing the chances of finding a recombinant with the target segment from the donor line moved to the recipient line. The closer the linkage, the more useful the marker, as recombination is less likely to occur between the marker and the gene causing the trait, which can result in false positives. Having flanking markers decreases the chances that false positive selection will occur as a double recombination event would be needed. The ideal situation is to have a marker in the gene itself, so that recombination cannot occur between the marker and the gene. Such a marker is called a 'perfect marker'.

When a gene is introgressed by MAS, it is not only the gene that is introduced but also the flanking regions (Gepts. (2002). *Crop Sci;* 42: 1780-1790). This is referred to as "linkage drag." In the case where the donor plant is highly unrelated to the recipient plant, these flanking regions carry additional genes that may code for agronomically undesirable traits. This "linkage drag" may also result in reduced yield or other negative agronomic characteristics even after multiple cycles of backcrossing into the elite maize line. This is also sometimes referred to as "yield drag." The size of the flanking region can be decreased by additional backcrossing, although this is not always successful, as breeders do not have control over the size of the region or the recombination breakpoints (Young et al. (1998) *Genetics* 120:579-585). In classical breeding it is usually only by chance that recombinations are selected that contribute to a reduction in the size of the donor segment (Tanksley et al. (1989). *Biotechnology* 7: 257-264). Even after 20 backcrosses in backcrosses of this type, one may expect to find a sizeable piece of the donor chromosome still linked to the gene being selected. With markers however, it is possible to select those rare individuals that have experienced recombination near the gene of interest. In 150 backcross plants, there is a 95% chance that at least one plant will have experienced a crossover within 1 cM of the gene, based on a single meiosis map distance. Markers will allow unequivocal identification of those individuals. With one additional backcross of 300 plants, there would be a 95% chance of a crossover within 1 cM single meiosis map distance of the other side of the gene, generating a segment around the target gene of less than 2 cM based on a single meiosis map distance. This can be accomplished in two generations with markers, while it would have required on average 100 generations without markers (See Tanksley et al., supra). When the exact location of a gene is known, flanking markers surrounding the gene can be utilized to select for recombinations in different population sizes. For example, in smaller population sizes, recombinations may be expected further away from the gene, so more distal flanking markers would be required to detect the recombination.

The availability of integrated linkage maps of the maize genome containing increasing densities of public maize markers has facilitated maize genetic mapping and MAS. See, e.g. the IBM2 Neighbors maps, which are available online on the MaizeGDB website.

The key components to the implementation of MAS are: (i) Defining the population within which the marker-trait association will be determined, which can be a segregating population, or a random or structured population; (ii) monitoring the segregation or association of polymorphic markers relative to the trait, and determining linkage or association using statistical methods; (iii) defining a set of desirable markers based on the results of the statistical analysis, and (iv) the use and/or extrapolation of this information to the current set of breeding germplasm to enable marker-based selection decisions to be made. The markers described in this disclosure, as well as other marker types such as SSRs and FLPs, can be used in marker assisted selection protocols.

SSRs can be defined as relatively short runs of tandemly repeated DNA with lengths of 6 bp or less (Tautz (1989) *Nucleic Acid Research* 17: 6463-6471; Wang et al. (1994) *Theoretical and Applied Genetics,* 88:1-6) Polymorphisms arise due to variation in the number of repeat units, probably caused by slippage during DNA replication (Levinson and Gutman (1987) *Mol Biol Evol* 4: 203-221). The variation in repeat length may be detected by designing PCR primers to the conserved non-repetitive flanking regions (Weber and May (1989) *Am J Hum Genet.* 44:388-396). SSRs are highly suited to mapping and MAS as they are multi-allelic, codominant, reproducible and amenable to high throughput automation (Rafalski et al. (1996) Generating and using DNA markers in plants. In: *Non-mammalian genomic analysis: a practical guide.* Academic press. pp 75-135).

Various types of SSR markers can be generated, and SSR profiles from resistant lines can be obtained by gel electrophoresis of the amplification products. Scoring of marker genotype is based on the size of the amplified fragment. An SSR service for maize is available to the public on a contractual basis by DNA Landmarks in Saint-Jean-sur-Richelieu, Quebec, Canada.

Various types of FLP markers can also be generated. Most commonly, amplification primers are used to generate fragment length polymorphisms. Such FLP markers are in many ways similar to SSR markers, except that the region amplified by the primers is not typically a highly repetitive region. Still, the amplified region, or amplicon, will have sufficient variability among germplasm, often due to insertions or deletions, such that the fragments generated by the amplification primers can be distinguished among polymorphic individuals, and such indels are known to occur frequently in maize (Bhattramakki et al. (2002). *Plant Mol Biol* 48, 539-547; Rafalski (2002b), supra).

SNP markers detect single base pair nucleotide substitutions. Of all the molecular marker types, SNPs are the most abundant, thus having the potential to provide the highest genetic map resolution (Bhattramakki et al. 2002 *Plant Molecular Biology* 48:539-547). SNPs can be assayed at an even higher level of throughput than SSRs, in a so-called 'ultra-high-throughput' fashion, as they do not require large amounts of DNA and automation of the assay may be straight-forward. SNPs also have the promise of being relatively low-cost systems. These three factors together make SNPs highly attractive for use in MAS. Several methods are available for SNP genotyping, including but not limited to, hybridization, primer extension, oligonucleotide ligation, nuclease cleavage, minisequencing and coded spheres. Such methods have been reviewed in: Gut (2001) *Hum Mutat* 17 pp. 475-492; Shi (2001) *Clin Chem* 47, pp. 164-172; Kwok (2000) *Pharmacogenomics* 1, pp. 95-100; Bhattramakki and Rafalski (2001) Discovery and application of single nucleotide polymorphism markers in plants. In: R. J. Henry, Ed, *Plant Genotyping: The DNA Fingerprinting of Plants*, CABI Publishing, Wallingford. A wide range of commercially available technologies utilize these and other methods to interrogate SNPs including Masscode™ (Qiagen), Invader® (Third Wave Technologies), SnapShot® (Applied Biosystems), Taqman® (Applied Biosystems) and Beadarrays™ (Illumina).

A number of SNPs together within a sequence, or across linked sequences, can be used to describe a haplotype for any particular genotype (Ching et al. (2002), *BMC Genet.* 3:19 pp Gupta et al. 2001, Rafalski (2002b), *Plant Science* 162:329-333). Haplotypes can be more informative than single SNPs and can be more descriptive of any particular genotype. For example, a single SNP may be allele 'T' for a specific line or variety with increased cell wall digestibility, but the allele 'T' might also occur in the maize breeding population being utilized for recurrent parents. In this case, a haplotype, e.g. a combination of alleles at linked SNP markers, may be more informative. Once a unique haplotype has been assigned to a donor chromosomal region, that haplotype can be used in that population or any subset thereof to determine whether an individual has a particular gene. See, for example, WO2003054229. Using automated high throughput marker detection platforms known to those of ordinary skill in the art makes this process highly efficient and effective.

Many of the primers listed in FIG. 6 can readily be used as FLP markers to select for the gene locus on chromosome 1 controlling cell wall digestibility, owing to the presence of insertions/deletion polymorphisms. These primers can also be used to convert these markers to SNP or other structurally similar or functionally equivalent markers (SSRs, CAPs, indels, etc), in the same regions. One very productive approach for SNP conversion is described by Rafalski (2002a) *Current opinion in plant biology* 5 (2): 94-100 and also Rafalski (2002b) *Plant Science* 162: 329-333. Using PCR, the primers are used to amplify DNA segments from individuals (preferably inbred) that represent the diversity in the population of interest. The PCR products are sequenced directly in one or both directions. The resulting sequences are aligned and polymorphisms are identified. The polymorphisms are not limited to single nucleotide polymorphisms (SNPs), but also include indels, CAPS, SSRs, and VNTRs (variable number of tandem repeats). Specifically with respect to the fine map information described herein, one can readily use the information provided herein to obtain additional polymorphic SNPs (and other markers) within the region amplified by the primers listed in this disclosure. Markers within the described map region can be hybridized to BACs or other genomic libraries, or electronically aligned with genome sequences, to find new sequences in the same approximate location as the described markers.

In addition to SSR's, FLPs and SNPs, as described above, other types of molecular markers are also widely used, including but not limited to expressed sequence tags (ESTs), SSR markers derived from EST sequences, randomly amplified polymorphic DNA (RAPD), and other nucleic acid based markers.

Isozyme profiles and linked morphological characteristics can, in some cases, also be indirectly used as markers. Even though they do not directly detect DNA differences, they are often influenced by specific genetic differences. However, markers that detect DNA variation are far more numerous and polymorphic than isozyme or morphological markers (Tanksley (1983) *Plant Molecular Biology Reporter* 1:3-8).

Sequence alignments or contigs may also be used to find sequences upstream or downstream of the specific markers listed herein. These new sequences, close to the markers described herein, are then used to discover and develop functionally equivalent markers. For example, different physical and/or genetic maps are aligned to locate equivalent markers not described within this disclosure but that are within similar regions. These maps may be within the maize species, or even across other species that have been genetically or physically aligned with maize, such as rice, wheat, barley or sorghum.

In general, MAS uses polymorphic markers that have been identified as having a significant likelihood of co-segregation with cell wall digestibility. Such markers are presumed to map near a gene or genes that give the plant its cell wall digestibility phenotype, and are considered indicators for the desired trait, or markers. Plants are tested for the presence of a desired allele in the marker, and plants containing a desired genotype at one or more loci are expected to transfer the desired genotype, along with a desired phenotype, to their progeny. The means to identify maize plants that have increased cell wall digestibility by identifying plants that have a specified allele at any one of marker loci described herein, including PHM8098, PHM14801, PHM4175, PHM1783, PHM3364, PHM1730, PHM4359, SCW_04_5b, PHM9167, PHM13936, PHM15671, PHM14875, PHM11079, PHM15150, PHM1239, PHM9528, PHM14541, PHM2690, PHM1241 and PHM11733 are presented herein.

The interval presented herein finds use in MAS to select plants that demonstrate increased cell wall digestibility. Any marker that maps within the chromosome 1 interval defined by and including PHM13936 and PHM11733 can be used for this purpose. In addition, haplotypes comprising alleles at one or more marker loci within the chromosome 1 interval defined by and including PHM13936 and PHM11733 can be used to introduce increased cell wall digestibility into maize lines or varieties. Any allele or haplotype that is in linkage disequilibrium with an allele associated with increased cell wall digestibility can be used in MAS to select plants with increased cell wall digestibility.

EXAMPLES

The following examples are offered to illustrate, but not to limit, the appended claims. It is understood that the examples and embodiments described herein are for illustrative purposes only and that persons skilled in the art will recognize various reagents or parameters that can be altered without departing from the spirit of the invention or the scope of the appended claims.

Example 1

Identification and Isolation of the *Zea mays* Laccase-Like Gene

Of the genes identified thus far that are involved in plant cell wall formation in maize, the cellulose synthase (CesA) genes, CesA10, CesA11 and CesA12, along with another gene, brittle stalk-2 (Bk2), are of particular interest because of their involvement in secondary cell wall formation (Appenzeller, et al., (2004) "Cellulose synthesis in maize: isolation and expression analysis of the cellulose synthase (CesA) gene family"; *Cellulose* 11:287-299; Ching, et al., (2006) "Brittle stalk 2 encodes a putative glycosylphosphatidylinositol-anchored protein that affects mechanical strength of maize tissues by altering the composition and structure of secondary cell walls"; *Planta* 224:1174-1184). These four genes were used as a reference set to identify other genes with similar expression patterns. The validation of these genes rely on the similarity of their expression patterns to those from a reference set across a large number of libraries in the MPSS™ data set. Pioneer-DuPont has an extensive, proprietary collection of 227 maize tissue/treatment MPSS™ data sets that cover a wide range of plant structure and biology. The MPSS data were arrayed in a large table to facilitate correlation analyses. Pearson's correlation coefficients were calculated across 227 samples for pairs in a way that each pair consisted of one member from the reference and a second member from the remaining tags. In doing so a list of four R and R2 values for each subject tag hit was generated, one to each of the four reference genes (specifically to the MPSS tag for those genes). The four values were then averaged and ranked in descending order. Those at the top of the list have an expression pattern across the maize MPSS data sets that is most similar to the four reference genes. For purposes of this study, a minimum cutoff average R value of approximately 0.7 was established.

One MPSS tag SCW_04 had an average expression coefficient 0.82 when its expression patterns were compared to the expression patterns of the reference set of genes. The gene from which this tag originated was identified using proprietary and public genomic and transcript sequence resources. Its ORF (SEQ ID NO:41), translation (SEQ ID NO:42), and transcript (SEQ ID NO:43) were obtained. The polypeptide sequence (SEQ ID NO:42) was analyzed for similarity to all publicly available amino acid sequences contained in the "nr" database using the BLASTP algorithm provided by the National Center for Biotechnology Information (NCBI). The top hit, with an E-value of 0, was to a *Zea mays* "unknown" protein (NCBI GI No:194692196; SEQ ID NO:44). The next hit, also with an E-value of 0, was to an *Oryza sativa* laccase protein (NCBI GI No: 115452197; SEQ ID NO:45). SEQ ID NO:42 is 99.1% identical to SEQ ID NO:44 and 79.7% identical to SEQ ID NO:45, using the Clustal V method of alignment with default parameters. Multiple alignment of the sequences was performed using the Clustal method of alignment (Higgins and Sharp (1989) CABIOS. 5:151 153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

In addition, SEQ ID NO:41 was analyzed for similarity to marker sequences in the Pioneer-DuPont proprietary database using the BLASTN algorithm. The sequence is an exact hit to a marker positioned on chromosome 1 at 91.66 cM on the internally derived PHB map and is located on the B73 BAC b0519g14 (See FIG. 1).

Example 2

Phenotyping of Lines for NDFd

To obtain NDFd (neutral detergent fiber digestibility) using wet chemistry, stover samples are collected, dried, ground to 4 mm, and then ground again to 1 mm. Twenty grams of dried, ground tissue are used per sample. NDFd for each line is assessed using a standard two-stage Tilley and Terry IVDMD. In the first stage, a subsample is obtained and then incubated in NDF extraction buffer (Van Soest), which removes the soluble material. The remaining material per definition is the cell wall, which is synonymous to neutral detergent fiber (NDF). In the second stage, another subsample is obtained and then incubated in rumen fluid for 48 hours. The residue is then subjected to NDF extraction, yielding the undigested cell wall portion, or the undigested NDF (uNDF). To obtain NDFd values, the following equation is used:

(NDF−uNDF)/NDF

Example 3

Whole Genome Scan Association

An association mapping strategy was undertaken to identify markers associated with cell wall digestibility, as measured by NDFd, in maize. In this association analysis, a collection of 475 maize lines was analyzed by DNA sequencing at 4000-10000 genes (genetic loci). The lines encompassed elite germplasm, commercially released cultivars, and other public varieties.

A structure-based association analysis was used, where the population structure is controlled using marker data. The model-based cluster analysis software, Structure, developed by Pritchard et al., (*Genetics* 155:945-959 (2000)) was used with haplotype data for 880 elite maize inbreds at two hundred markers to estimate admixture coefficients and assign the inbreds to seven subpopulations. This reduces the occurrence of false positives that can arise due to the effect of population structure on association mapping statistics. Kuiper's statistic for testing whether two distributions are the same was used to test a given marker for association between haplotype and phenotype in a given subpopulation (Press et al., Numerical Recipes in C, second edition, Cambridge University Press, NY (2002)).

In one subpopulation consisting of 52 Stiff Stalk lines, a peak of significant marker-trait associations was observed on chromosome 1 (FIG. 2). Table 1 provides a listing of the maize markers significantly associated with NDF digestibility, as measured using wet chemistry, at p ≤0.01 level (see boxed region in FIG. 3). Positions are given in cM, with position zero being the first (most distal from the centromere) marker known at the beginning of the chromosome. These map positions are not absolute, and represent an estimate of map position based on the internally derived genetic map.

TABLE 1

Markers significantly associated with digestible NDF at p ≤ 0.01 in the Stiff Stalk subpopulation

| Marker Locus | Relative map position (cM) PHB | P-Value |
|---|---|---|
| PHM13936 | 85.14 | 0.0095 |
| PHM15671 | 85.65 | 0.0038 |
| PHM14875 | 86.29 | 0.0078 |
| PHM8098 | 89.71 | 8.00E−04 |
| PHM14801 | 90.52 | 7.80E−04 |
| PHM4175 | 90.79 | 2.08E−04 |
| PHM1783 | 91.29 | 4.80E−05 |
| PHM3364 | 91.61 | 1.70E−04 |
| PHM1730 | 91.69 | 1.12E−04 |
| PHM4359 | 91.69 | 4.22E−04 |
| PHM11079 | 91.96 | 0.0034 |
| PHM9167 | 93.09 | 4.20E−04 |
| PHM15150 | 93.09 | 0.0016 |
| PHM1239 | 97.67 | 0.0073 |
| PHM9528 | 97.67 | 0.0038 |
| PHM14541 | 98.54 | 0.004 |
| PHM2690 | 98.91 | 0.005 |

TABLE 1-continued

Markers significantly associated with digestible NDF
at p ≤ 0.01 in the Stiff Stalk subpopulation

| Marker Locus | Relative map position (cM) PHB | P-Value |
|---|---|---|
| PHM11733 | 99.88 | 0.0072 |
| PHM1241 | 99.9 | 0.0039 |

Example 4

Candidate Gene Association

Primers (SEQ ID NO:46 and SEQ ID NO:47), were designed from the genomic sequence (SEQ ID NO:49) comprising the laccase-like gene (SEQ ID NO:41), to amplify an untranslated region near the *Zea mays* laccase-like locus from each of the 52 stiff stalk inbred lines. The locus amplified by the primers was referred to as marker SCW__04__5b, the sequence of which is represented by SEQ ID NO:48. Genotypes were obtained for the 52 inbred lines at this locus and the polymorphic loci were tested for association with NDFd (as determined using wet chemistry) using software tools developed in-house. Significant associations with NDFd at this locus were observed (FIG. 5). FIG. 5 is a table showing the informative SNP positions at the SCW__04__5b marker locus, the number of inbreds with and without a particular SNP, trait means, and p-values for association with SNPs (P asymptotic and P permutation).

Example 5

Marker Framework and Use for Marker Assisted Selection

A set of common markers can be used to establish a framework for identifying markers in the QTL interval. Table 2A and Table 2B show markers that are in a consistent position relative to one another on the PHB internally derived map, the IBM2 neighbors genetic map, and the current physical map (FIG. 1). Markers shown in Table 2A which reside at a particular BAC in FIG. 1 are identified by an asterisk in the BAC number box in FIG. 1. Table 2B shows the order of the sequenced BACs on the physical map arrangement (FIG. 1) (obtained from the Maize Genome Browser, which is publicly available on the internet) that assemble to the region defined by and including PHM13936 (SEQ ID NO:94) and PHM11733 (SEQ ID NO:104). The positions of the PHM markers described herein are indicated by an asterisk (*) in Table 2B and FIG. 1 and further explained in Table 2A.

TABLE 2A

Molecular marker positions on the
PHB map and the IBM2 Neighbors map.

| BAC Number (FIG. 1) | BAC Name | Marker Locus (SED ID NO:) | Marker locus PHB map position (cM) | Marker locus IBM2 neighbors |
|---|---|---|---|---|
| B3 | c0213M06 | PHM13936 (94) | 85.1 | n/a |
|  |  | PHM15671 (95) | 85.7 | n/a |
| B7 | c0292P10 | PHM14875 (96) | 86.3 | n/a |
| B30 | b0333N05 | PHM8098 (1) | 89.7 | n/a |
| B 44 | c0114n02 | PHM14801 (2) | 90.5 | n/a |

TABLE 2A-continued

Molecular marker positions on the
PHB map and the IBM2 Neighbors map.

| BAC Number (FIG. 1) | BAC Name | Marker Locus (SED ID NO:) | Marker locus PHB map position (cM) | Marker locus IBM2 neighbors |
|---|---|---|---|---|
| B 45 | b0377g04 | PHM4175 (3) | 90.8 | 226.4 |
|  |  | umc1397 | 90.9 | 226.4 |
| B 47 | c0069K04 | PHM1783 (4) | 91.3 | n/a |
|  |  | AY110052 | n/a | 229.6 |
| B 48 | c0115H21 | PHM3364 (5) | 91.6 | n/a |
| B 50 | b0434D02 | PHM1730 (6) | 91.7 | n/a |
|  |  | csu859 | n/a | 242.2 |
| B 51 | b0519G14 | PHM4359 (7) | 91.7 | n/a |
|  |  | PHM11079 (97) | 92.0 | n/a |
| B 53 | c0544P21 | PHM9167 (8) | 93.1 | n/a |
| B 54 | c0287J07 | PHM15150 (98) | 93.1 | n/a |
| B 92 | b0334G06 | PHM2690 (102) | 98.9 | n/a |
| B 95 | c0262C05 | PHM9528 (100) | 97.7 | n/a |
| B 99 | b0385K15 | PHM14541 (101) | 98.5 | n/a |
| B 106 | c0118H21 | PHM1239 (99) | 97.7 | n/a |
|  |  | PHM1241 (103) | 99.9 | n/a |
| B 107 | c0548B17 | PHM11733 (104) | 99.9 | 282.6 |

TABLE 2B

Order of the sequenced BACs on the physical map arrangement
(FIG. 1) that assemble to the region defined by and including
PHM13936 (SEQ ID NO: 94) and PHM11733 (SEQ ID NO: 104).

| BAC Number | BAC Name | BAC Number | BAC Name | BAC Number | BAC Name |
|---|---|---|---|---|---|
| B1 | b0224H06 | B2 | b0389I23 | B3* | c0213M06 |
| B4 | b0119J19 | B5 | b0331F15 | B6 | b0138N01 |
| B7* | c0292P10 | B8 | c0418N12 | B9 | c0085B05 |
| B10 | b0614H07 | B11 | c0029E01 | B12 | b0574E09 |
| B13 | b0596I11 | B14 | b0588B07 | B15 | c0131J12 |
| B16 | b0342D19 | B17 | c0111N24 | B18 | c0196C18 |
| B19 | c0289G12 | B20 | c0537D21 | B21 | c0149E11 |
| B22 | c0151I15 | B23 | c0170O09 | B24 | c0131F12 |
| B25 | c0432D07 | B26 | c0384F14 | B27 | c0375C13 |
| B28 | c0107K02 | B29 | c0427A19 | B30* | b0333N05 |
| B31 | c0261A24 | B32 | c0261C23 | B33 | c0128M10 |
| B34 | c0548B14 | B35 | b0189G18 | B36 | c0090M09 |
| B37 | c0403A04 | B38 | c0295D18 | B39 | c0527O01 |
| B40 | c0274L13 | B41 | c0214I05 | B42 | c0104b23 |
| B43 | b0372d12 | B44* | c0114n02 | B45* | b0377g04 |
| B46 | c0526O03 | B47* | c0069K04 | B48* | c0115H21 |
| B49 | c0294F02 | B50* | b0434D02 | B51* | b0519G14 |
| B52 | c0521O11 | B53* | c0544P21 | B54* | c0287J07 |
| B55 | c0010M04 | B56 | c0528K09 | B57 | b0431O07 |
| B58 | b0119M07 | B59 | c0333E23 | B60 | b0495N19 |
| B61 | c0011I14 | B62 | c0296P24 | B63 | c0052E13 |
| B64 | b0331H10 | B65 | c0474A17 | B66 | c0463M16 |
| B67 | c0297N05 | B68 | b0129G22 | B69 | c0264L18 |
| B70 | c0410E21 | B71 | c0236F19 | B72 | b0195G24 |
| B73 | c0189O12 | B74 | c0152F12 | B75 | b0627D20 |
| B76 | c0046A19 | B77 | b0302L08 | B78 | c0117B15 |
| B79 | c0455E22 | B80 | c0455A06 | B81 | b0340C10 |
| B82 | c0403A03 | B83 | c0280C14 | B84 | b0435E05 |
| B85 | c0266M24 | B86 | b0397H06 | B87 | c0378I14 |
| B88 | c0315D23 | B89 | c0273C12 | B90 | b0158A07 |
| B91 | c0173I11 | B92* | b0334G06 | B93 | b0474J04 |
| B94 | c0472K14 | B95* | c0262C05 | B96 | c0215N19 |
| B97 | c0157G02 | B98 | c0202E13 | B99* | b0385K15 |
| B100 | b0366G20 | B101 | c0014D03 | B102 | b0195A14 |
| B103 | c0438M13 | B104 | c0076G09 | B105 | b0286H14 |
| B106* | c0118H21 | B107* | c0548B17 | B108 | c0113A18 |
| B109 | c0149M05 | B110 | c0112J07 | B111 | c0529E03 |

BACs that include molecular markers are indicated by an asterisk (*).

Closely linked markers flanking the locus of interest that have alleles in linkage disequilibrium with a favorable allele at that locus may be effectively used to select for progeny plants with increased cell wall digestibility. Thus, the markers described herein, such as those listed in Table 2A, as well as other markers genetically or physically mapped to the same chromosomal segment, may be used to select for maize plants with increased cell wall digestibility. Typically, a set of these markers will be used, (e.g., 2 or more, 3 or more, 4 or more, 5 or more) in the flanking region above the gene and a similar set in the flanking region below the gene. Optionally, as described above, a marker within the actual gene and/or locus may also be used. The parents and their progeny are screened for these sets of markers, and the markers that are polymorphic between the two parents are used for selection. The most proximal polymorphic markers to the gene or locus are used to select for the gene or locus, and the more distal polymorphic markers are used to select against the gene or locus. In an introgression program, this allows for selection of the gene or locus genotype at the more proximal polymorphic markers and selection for the recurrent parent genotype at the more distal polymorphic markers.

All plants to be used in the breeding program, such as a gene introgression program, are screened with markers. The markers disclosed herein or equivalent markers on the same chromosomal segment may be used.

An analysis of inbreds grouped by the presence or absence of a good haplotype supports this invention because it is believed that marker assisted selection for the good haplotype is correlative to enhanced digestibility and silage quality.

Example 6

Association of a Genetic Locus with Cell Wall Digestibility in Segmental Introgression Lines Segmental introgression lines have been used to study the association between genetic loci and desirable or undesirable plant characteristics (Holtan, H. and Hake, S. (2003) *Genetics*, 165(3):1541-50 and Fridman et al., (2004) *Science*, 305 (5691) 1786-9).

In this invention, a set of 48 segmental introgression lines was developed by backcrossing an early lodent/SSS inbred line with very good neutral detergent fiber digestibility (NDFd) as the recurrent parent with an early lodent inbred line with very poor NDFd as the donor parent. The lines of the BC3F2 generation were genotyped using 240 SNP markers spread across the whole genome. The average segment size of the donor parent in each segmental introgression line was 30 to 50 cM. Segments were overlapping between adjacent lines.

Stalk segments of the 48 lines were harvested at silage stage at three field locations in Germany and France in 2007 with two replicates per location, dried and ground to a fine powder and analyzed for NDFd using NIRS. The mean NDFd value across the three locations and location means from each location were used for QTL analyses. QTL analyses were performed with the mapping software MaxQTL using composite interval mapping with simple interval mapping selection of cofactors. The significance threshold for declaring a QTL was set to 0.01. Identity by descent information to key founders was used for mapping with a minimum founder probability threshold of 0.05. Map positions were defined as in the Pioneer High Density Map version 1.4.

A QTL peak with a likelihood ratio of 7.9 was found on Chromosome 1 at position 90 cM using location means from one location in France. A peak with a likelihood ratio of 5.7 was detected at 90 cM using means across three locations and a smaller peak was detected using location means from one location in Germany, however, those two peaks were below the significance threshold. At the second location in Germany no indication for a QTL was detected.

What is claimed:

1. A method of identifying a maize plant that displays increased cell wall digestibility, the method comprising detecting in the germplasm of the maize plant the presence of at least one allele of a marker locus wherein:
   a. the marker locus is located within a chromosomal interval comprising and flanked by PHM8098 and PHM9167; and
   b. the at least one allele is associated with increased cell wall digestibility.

2. The method of claim 1, wherein the marker locus is SCW_04_5b.

3. The method of claim 1, wherein the maize plant belongs to the Stiff Stalk heterotic group.

4. A method of identifying a maize plant that displays increased cell wall digestibility, the method comprising detecting in the germplasm of the maize plant a halotype comprising alleles at one or more marker loci, wherein:
   a. the one or more marker loci are located within a chromosomal interval comprising and flanked by PHM8098 and PHM9167; and
   b. the halotype is associated with increased cell wall digestibility.

5. The method of claim 4 wherein the one or more marker loci are located within a chromosomal interval comprising and flanked by PHM8098 and PHM9167.

6. The method of claim 4, wherein the maize plant belongs to the Stiff Stalk heterotic group.

7. A method of marker assisted selection comprising:
   a. obtaining a first maize plant having at least one allele of a marker locus, wherein the marker locus is located within a chromosomal interval comprising and flanked by PHM8098 and PHM9167 and the allele of said marker locus is associated with increased cell wall digestibility,
   b. crossing said first maize plant to a second maize plant;
   c. evaluating the progeny for at least said allele; and
   d. selecting progeny plants that possess at least said allele.

8. The method of claim 1, further comprising after the detecting step the step of introgressing the at least one allele into a maize plant.

9. The method of claim 4, further comprising after the detecting step the step of introgressing the haplotype into a maize plant.

* * * * *